(12) United States Patent
Hattori et al.

(10) Patent No.: US 8,691,951 B2
(45) Date of Patent: Apr. 8, 2014

(54) TYPE I-TYPE IV COLLAGEN HYBRID GEL

(75) Inventors: Shunji Hattori, Tokyo (JP); Yoh-ichi Koyama, Tokyo (JP); Hitomi Fujisaki, Tokyo (JP); Kiyotoshi Sekiguchi, Suita (JP); Sugiko Futaki, Suita (JP); Ryoko Sato, Suita (JP)

(73) Assignees: Japan Institute of Leather Research, Tokyo (JP); Osaka University, Osaka (JP)

( * ) Notice: Subject to any disclaimer, the term of this patent is extended or adjusted under 35 U.S.C. 154(b) by 369 days.

(21) Appl. No.: 13/027,088

(22) Filed: Feb. 14, 2011

(65) Prior Publication Data

US 2012/0208761 A1 Aug. 16, 2012

(51) Int. Cl.
| | |
|---|---|
| *A61K 38/17* | (2006.01) |
| *A61K 47/48* | (2006.01) |
| *C07K 1/00* | (2006.01) |
| *C07K 14/00* | (2006.01) |
| *C07K 16/00* | (2006.01) |
| *C07K 17/00* | (2006.01) |
| *C12M 1/22* | (2006.01) |
| *C12M 3/00* | (2006.01) |
| *A61K 38/39* | (2006.01) |

(52) U.S. Cl.
USPC .................. 530/356; 435/305.1; 514/17.2

(58) Field of Classification Search
None
See application file for complete search history.

(56) References Cited

U.S. PATENT DOCUMENTS

| 5,667,961 A | 9/1997 | Bernard et al. |
|---|---|---|
| 2004/0018623 A1* | 1/2004 | Rosenberg ............ 435/372 |
| 2009/0012628 A1 | 1/2009 | Shortkroff et al. |

FOREIGN PATENT DOCUMENTS

| JP | 37-14426 B2 | 11/2005 |
|---|---|---|
| WO | WO 2008/100226 A1 | 8/2008 |

OTHER PUBLICATIONS

Hughes et al. Matrigel: A complex protein mixutre required for optimal growth of cell culture. Proteomics, 2010, vol. 10, pp. 1886-1890.*

"Development of technology for creating a model cell for the research/ development of technology for controlling a differentiation induction of ES cell using an artificial basement membrane of which molecular composition is optimized" Mid Annual Report 2008, NEDO, 2007-2009.

Fuji, "The Effect of Amines Added to an Alkali-Pretreatment on the Solubilisation of Collagen and on the Properties of Gelatin", Hoppe-Seyler's Z. Physiol., Chem. vol. 350, pp. 1257-1265, Oct. 1969.

Fujisaki et al., "Keratinocyte Apoptosis on Type I Collagen Fibrils is Prevented by Erk1/2 Activation under High Calcium Condition" Connective Tissue Research, vol. 48, pp. 159-169, 2007.

Fujisaki et al., "Keratinocyte Apoptosis on Type I Collagen Gel Caused by Lack of Laminin May 10, 2011 Deposition and Akt Signaling", Experimental Cell Research, vol. 280, pp. 255-269, 2002.

Muraoka et al., "Three Polypeptides with Distinct Biochemical Properties Are Major α Chain-Size Components of Type IV Collagen in Bovine Lens Capsule", J. Biochem., vol. 114, pp. 358-362, 1993.

Nishiyama et al., "Growth Rate of Human Fibroblasts is Repressed by Culture within Reconstituted Collagen Matrix but not by the Culture on the Matrix" Matrix, vol. 9, pp. 193-199, 1989.

Sage et al., "Structural Studies on Human Type IV Collagen", The Journal of Biological Chemistry, vol. 254, No. 19, pp. 9893-9900, Issue of Oct. 10, 1979.

Daoud et al., "Long-term in vivo human pancreatic islet culture using three-dimensional microfabricated scaffolds," Biomaterials (2001) vol. 32, pp. 1536-1542.

Dickinson et al., "Reconstructing the differentiation niche of embryonic stem cells using biomaterials," Macromol. Biosci. (2011) vol. 11, pp. 36-49.

European Search Report issued Jul. 7, 2011, in European Patent Application No. 11001264.8.

Kubota et al., "Role of laminin and basement membrane in the morphological differentiation of human endothelial cells into capillary-like structures," The Journal of Cell Biology (Oct. 1988) vol. 107, pp. 1589-1598.

Zhou et al,. "Embryoid bodies formation and differentiation from mouse embryonic stem cells in collagen/Matrigel scaffolds," J. Genet. Genomics (2010) vol. 37, pp. 451-460.

* cited by examiner

*Primary Examiner* — Marcela M Cordero Garcia
(74) *Attorney, Agent, or Firm* — Birch, Stewart, Kolasch & Birch, LLP

(57) ABSTRACT

It is an object of the present invention to provide a Type I-Type IV collagen hybrid gel, which maintains characteristics of a Type IV collagen and is superior in gel strength. It is the Type I-Type IV collagen hybrid gel obtained by mixing 100 to 500 parts by mass of the Type I collagen having fibrosis ability, relative to 100 parts by mass of the Type IV collagen having gelling ability. A three-dimensional structure is formed, where a membrane-like substance by the Type IV collagen is formed onto a fibrous substance by the Type I collagen, so as to be able to provide cell culture environment approximate to a basement membrane of a living body.

11 Claims, 9 Drawing Sheets

3. Beads held on a gel
2. Type I-Type IV collagen hybrid gel
1. Beads fallen on the bottom surface A, Type I-Type IV collagen hybrid B, Type I collage C, Hybrid gel of Type I collagen and Type IV collagen not having gelling ability Fig.4
Fig.4 A
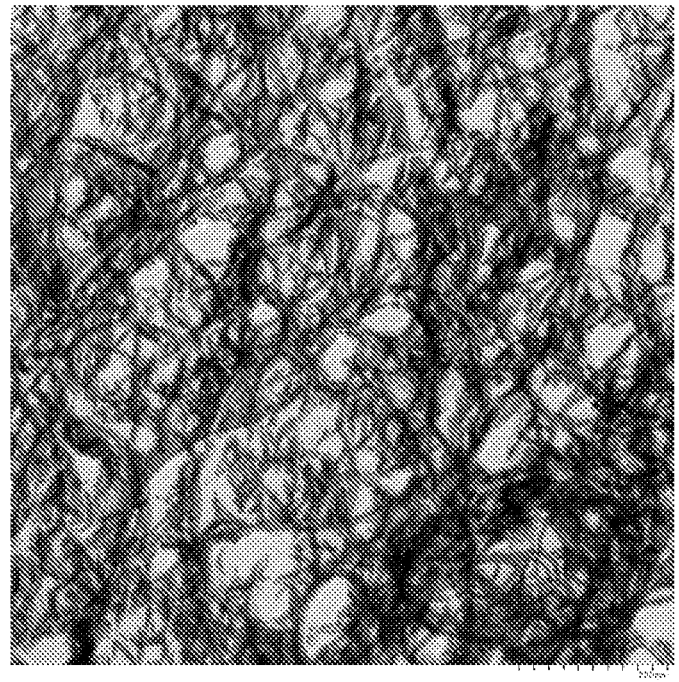
Fig.4 B
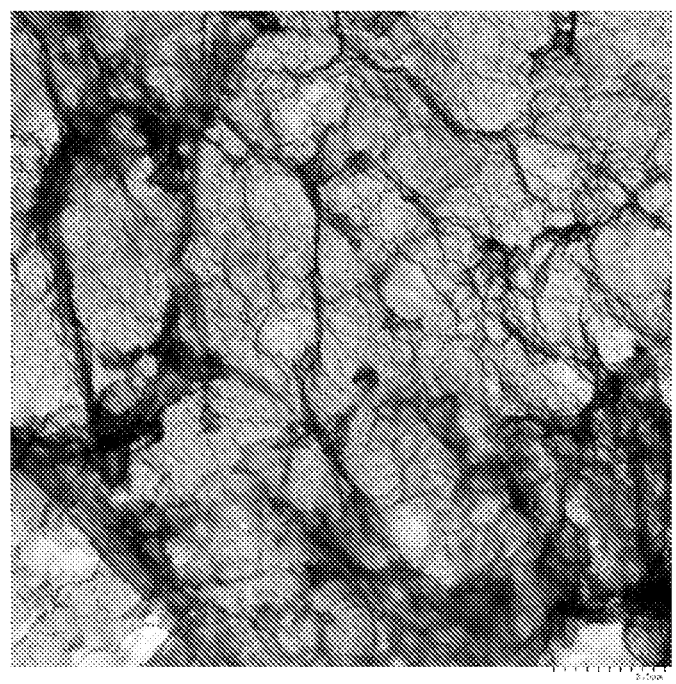

A, Addition of laminin 111 to Type I- Type IV collagen

B, Addition of laminin 511 to Type I -Type IV collagen

TYPE I-TYPE IV COLLAGEN HYBRID GEL

TECHNICAL FIELD

The present invention relates to a Type I-Type IV collagen hybrid gel, which can reproduce physiological function of a basement membrane by the Type IV collagen, and superior in gel strength, and a production method for the hybrid gel, along with a cell culture plate coated with the hybrid gel or the like.

BACKGROUND OF THE INVENTION

A body of an animal is composed of combination of four kinds of tissue types called an epithelial tissue, a connective tissue, a muscle tissue and a nervous tissue, and the epithelial tissue or the muscle tissue is mainly composed of a cell, while a main constituent of the connective tissue is an extracellular matrix called stroma having a collagen fiber as a main component. In addition, there is present a sheet-like extracellular matrix called a basement membrane between the epithelial tissue and connective tissue, and a cell composing the muscle tissue is also covered with the basement membrane at the periphery, and a blood vessel is also backed with the basement membrane in an endothelial cell thereof. Further, most of cells composing a multicellular organism have the basement membrane as an anchorage thereof, such that a nervous cell or the Schwann cell enveloping, for example, an axon of a peripheral nerve also has the basement membrane as the anchorage thereof, or the like. The extracellular matrix is required for growth or survival of a cell; for example, an animal cell not only cannot grow but also self-destructs with generating apoptosis, unless an animal cell can adhere to a culture dish and form the anchorage. This phenomenon is called anchorage dependence of cell growth, and this phenomenon is observed in almost all cells composing the multicellular organism, except a malignant cancer cell or a blood corpuscle cell.

The basement membrane to be the anchorage in such cell culture is the extremely thin sheet-like extracellular matrix with a thickness of about 100 nm, and is composed of a Type IV collagen, a laminin, a nidogen, a heparan sulfate proteoglycan or the like, which compose a three-dimensional structure by binding in a complex way. For example, the Type IV collagen is a main constituent bearing morphology maintenance of the basement membrane, and forms a tetramer cross-linked by a disulfide bond at an N-terminal region, while associates in an end-to-end type at a spherical region of a C-terminal, thus constructs a two-dimensional network structure through this association of N-terminal region and the C-terminal region. In addition, the laminin is a hetero trimer molecule, where three subunit chains called $\alpha$, $\beta$ and $\gamma$ are associated, and is a component of the basement membrane having a cross shape. There are present 11 kinds of subunits in total, wherein there are present $\alpha1$ to $\alpha5$ in the $\alpha$-chain, $\beta1$ to $\beta3$ in the $\beta$ chain, and $\gamma1$ to $\gamma3$ in the $\gamma$ chain. There have been known 15 kinds of laminins at present time by a combination of these subunits, names thereof are called by a constitution of the subunit chains. The three subunit chains have a common coiled coil domain to form the hetero trimer by association in this region. On the other hand, the N-terminal region of each subunit has affinity mutually, and is self-organized to the basement membrane by association in this region. It should be noted that laminin self-associated at the base surface acquires physical strength, by bonding with the Type IV collagen via nidogen and being backed with the network structure, which the Type IV collagen creates independently by self-association. Further, the structure thereof is stabilized by adding heparan sulfate proteoglycan, and by mutual action between the basement membrane molecules, and an intermolecular cross-linking by a disulfide bonding or a non-disulfide bonding.

Conventionally, research on the extracellular matrix has been carried out mainly on a collagen. In the mammals, about 30 kinds of genetically different collagens have been found, and they are named a Type I, a Type II, a Type III or the like in the order of discovery. Each of them differs in a structure, function and distribution, however, it has a right-handed helical structure, where three polypeptide chains called the $\alpha$-chain are wound mutually, and the polypeptide chain is common in having a basic structure composed of repetition of Gly-X—Y (wherein X and Y represent an arbitrary amino acid). It should be noted that in the Type I collagen, telopeptide, which is a non-helical region, is present at the both ends of the three-helical region.

A major collagen composing the basement membrane is the Type IV collagen. It forms the helical structure of the three chains similarly as the Type I collagen, however, it differs from the Type I collagen in that it has a part, where the Gly-X—Y structure interrupts. In addition, the Type IV collagen has a 7S region containing many cysteine residual groups at the N terminal, and a non-collagen helical region (NC1 region) at the molecular C terminal, which are important regions in that the two-dimensional network structure of the Type IV collagen is formed via the 7S region and the NC1 region.

In general, a collagen of the connective tissue of an animal is easily extracted by heat treatment, however, in this case, the specific three-helical structure thereof is destructed by thermal denaturation of the collagen to become a gelatin state. A collagen is generally poorly soluble in a state that the stereo structure thereof is maintained as it is, and a particular method becomes necessary to obtain the collagen as a solution. As an extraction method for the Type IV collagen, there have been known a method for extracting the Type I, III, V and IV collagens contained in a placenta by pepsin treatment using the placenta as a material, and then purifying the Type IV collagen by salt fractionation, a column or the like (NON-PATENT LITERATURE 1: Sage H, etal. J. Biol. Chem. 254, 9893-9900 (1979)); or a method for extracting the Type IV collagen in a non-enzymatic way in an acidic solution from a lens capsule of an animal eyeball only composed of almost the Type IV (NON-PATENT LITERATURE 2: Muraoka, M and Hayashi, T., J. Biochem. 114, 358-362 (1993)).

On the other hand, among various collagens, for example, the Type I collagen is a major constituent of the connective tissue such as skin, tendon, bone or the like of an animal, having a helical structure of about 300 nm, where three polypeptide chains are bound mutually. A slender fiber is created by association of these three-helical bodies in mutually shifting by 1/4.4, which further forms a bundle by alignment in parallel, and forms a collagen fiber which endures against strong tension. As an extraction method for the Type I collagen, there has been known an extraction method with an acidic solution or by enzyme treatment using bone or skin or the like of an animal as a material (PATENT LITERATURE 1: JP-B-37-14426); or a method for solubilization by alkali treatment (NON-PATENT LITERATURE 3: Fujii, T. Hoppe-Seyler's Z. Physiol., Chem. 350, 1257-1265 (1969)) or the like.

The Type I collagen or Type IV collagen is a constituent of the extracellular matrix, and acts as a cell adhesion factor. This is the reason for carrying out collagen coating of the cell culture plate in cell culture. On the other hand, the Type I collagen or Type IV collagen differs in fibrosis ability or gel forming ability or others depending on the extraction method thereof, and shape of the collagen in the coated layer differs depending of the collagen coating method.

There is a report that, although cell doubling time was same in the collagen coated dish and the three-dimensional collagen fiber gel, extension by 1.5 times and significant growth inhibition were observed in a cell-containing three-dimensional collagen gel, when a fibroblast was cultured using three kinds of the cell culture plates, that is, one (a collagen coated dish) obtained by putting a hydrochloric acid solution of the Type I collagen treated with pepsin on the surface of the cell culture plate, and drying with sterile air flow at 25° C.; one (the three-dimensional collagen fiber gel) obtained by stirring the hydrochloric acid solution of collagen with a DMEM culture medium containing penicillin, streptomycin, FBS-containing DMEM culture medium, and putting this on the cell culture plate and incubating this at 37° C. for 6 hours under $CO_2$ condition; and one (the cell-containing three-dimensional collagen gel) obtained by mixing the collagen culture medium solution and a cell suspension solution, and immobilizing onto the cell culture plate(NON-PATENT LITERATURE 4: Nishiyama, T. et al. Matrix, 9, 193-199 (1989)).

In addition, apoptosis is induced in a fibrous collagen, when a keratinocyte was cultured by the non-fibrous collagen obtained by coating a phosphoric acid buffer solution not containing calcium and magnesium of the Type I collagen onto the cell culture plate, and mounting at room temperature for 2 hours, and by the fibrous collagen obtained by putting a PBS (−) solution of the Type I collagen onto the cell culture plate and incubating at 37° C. for 2 hours to associate in a fibrous form (NON-PATENT LITERATURE 5: Fujisaki, H. and Hattori, S., Exp. Cell. Res. 280, 255-269 (2002), NON-PATENT LITERATURE 6: Fujisaki, H. et al. Connect. Tissue Res. 48, 159-169 (2007)).

It should be noted that there is "Matrigel" as the cell culture plate coated with a basement membrane component. The "Matrigel" is composed of an extract of sarcoma, which excessively produces a basement membrane molecule called EHS (Engelbreth-Holm-Swarm) sarcoma of a mouse, and further, is one blended with laminin, heparan sulfate proteoglycan, entactin or the like.

DISCLOSURE OF THE INVENTION

Problems to be Solved by the Invention

When cell culture is carried out using the cell culture plate coated with a collagen, a cultured cell adheres onto a collagen molecule via an integrin, which is a collagen receptor at the surface, and grows on the cell culture plate. Presence of the basement membrane is essential for maintaining, differentiation or growth of a stem cell of the epithelial cell, and it is desirable to use the cell culture plate coated with the Type IV collagen, which is a main component of the basement membrane.

In addition, a collagen forms a three-dimensional structure depending on a production method, and difference occurs in growth or differentiation of a cultured cell depending on whether it takes the three-dimensional structure or not, even when the cell culture plate is coated. The basement membrane is composed of Type IV collagen as a main component thereof in a widely spread network state, and it can form cell growth environment further approximate to the basement membrane of a living body, if it can reproduce the network structure of Type IV collagen at the surface of the cell culture plate.

However, because Type IV collagen is produced by a placenta or a lens capsule of an eyeball of an animal as an extraction raw material, production in a large quantity is difficult. For example, a commercially available a registered trade name "Matrigel" is an extract from EHS sarcoma of a mouse, however, use of Type IV collagen extracted from a normal body is preferable in culture of a normal cell, and thus availability of the raw material is not easy. In addition, Type IV collagen cannot form the network structure by gelling, because of weak molecular interaction depending on an extraction method, and even in the case of gelling, it does not form the network structure unless it is stood still at a temperature of 4° C. for five days or longer. Therefore, formation of the three-dimensional structure requires a long period of time, and thus formation of the substantial three-dimensional structure by the Type IV collagen is not easy. Therefore, it has been desired to develop a culture substrate having characteristics of the Type IV collagen, which can reduce use amount of the Type IV collagen and having characteristics of the Type IV collagen as a constituent of the basement membrane, and can form the three-dimensional structure simply and conveniently and having characteristics of the Type IV collagen as a constituent of the basement membrane.

On the other hand, because the Type I collagen has high gel strength and is relatively easily carried out extraction or purification, it can be used widely as a substrate of three-dimensional culture of a collagen.

However, the Type I collagen does not have the function as the basement membrane, and requires to maintain physiological activity of the basement membrane and compose the stable three-dimensional gel, in order to maintain the culture of the ES cell or a cell differentiated and introduced therefrom, and further to culture or grow the tissue stem cell separated from various organs.

In addition, even if enhancement of gel strength is tried by mixing the Type I collagen and the Type IV collagen, the Type I collagen forms an associated body at 37° C. to provide a gel, and lower temperature than this provides a solution with molecular dispersion, and cannot form an associated body; on the other hand, association temperature of the Type IV collagen is 4° C., that is, lower than 37° C. Practically, there has not been known the hybrid gel composed of the Type I collagen and the Type IV collagen, and there is also not present a method for forming the three-dimensional gel by the Type I collagen and the Type IV collagen.

Therefore, it has been desired to develop the Type I-Type IV collagen hybrid gel, which can form a uniform three-dimensional structure by mixing the Type I collagen and the Type IV collagen with different association temperature, and exerting the function of the Type IV collagen.

In addition, the basement membrane becomes the anchorage of a cell of various organs such as ES cell and iPS cell, to adjust growth or differentiation thereof. If environment approximate to the basement membrane of a living body can be formed as the cell culture plate, the culture much nearer to living body environment can be carried out. Because such a basement membrane contains the laminin as an essential component other than the Type IV collagen, it is preferable that the laminin is contained also in the Type I-Type IV collagen hybrid gel to be used.

However, although the Type I collagen becomes fibrous by association, bonding force of laminin to such a fibrous collagen is weak. Therefore, it is desired to develop the Type I-Type IV collagen hybrid gel composed of the hybrid gel obtained by mixing the Type I collagen and the Type IV collagen and bonded with laminin, along with the cell culture plate, which is obtained by using such a hybrid gel.

In view of the above present state, it is an object of the present invention to provide the Type I-Type IV collagen hybrid gel, which maintains characteristics as a constituent of the basement membrane of the Type IV collagen, is superior in gel strength and can form the three-dimensional structure.

In addition, it is an object of the present invention to provide a production method for the Type I-Type IV collagen hybrid gel, characterized by mixing the Type I collagen and the Type IV collagen, and forming the three-dimensional gel.

Further, it is an object of the present invention to provide the cell culture plate coated with the Type I-Type IV collagen hybrid gel at the surface of the cell culture plate.

Furthermore, it is an object of the present invention to provide an artificial basement membrane composed of the Type I-Type IV collagen hybrid gel.

Means for Solving the Problem

The present inventors have intensively studied a way to solve the above problems and found that the three-dimensional gel, where a membrane-like structure by the Type IV collagen is bound to a fibrous structure by the Type I collagen, can be formed in a short period of time, in mixing a specific Type I collagen and a specific Type IV collagen under specific condition; such a hybrid three-dimensional gel has characteristics approximate to that of the Type IV collagen contained in the basement membrane, in spite of reduced use amount of the Type IV collagen; this hybrid three-dimensional gel can bind the laminin corresponding to blending amount of the Type IV collagen, different from the Type I collagen and thus can form cell culture environment further approximate to a basement membrane; and the cell culture plate coated with such a hybrid gel onto the cell culture plate can become the cell culture plate extremely approximate to the basement membrane, because the three-dimensional gel composed of the Type I collagen and the Type IV collagen is formed; and have thus completed the present invention.

That is, the present invention provides the Type I-Type IV collagen hybrid gel, composed by mixing 100 to 500 parts by mass of the Type I collagen having fibrosis ability, relative to 100 parts by mass of the Type IV collagen having gelling ability.

In addition, the present invention provides the above Type I-Type IV collagen hybrid gel, characterized in that a membrane-like substance by the Type IV collagen is bound to a fibrous structure by the Type I collagen.

Further, the present invention provides the Type I-Type IV collagen hybrid gel, characterized by containing the laminin.

The present invention provides a cell culture plate, characterized in that the Type I-Type IV collagen hybrid gel is coated onto a support for cell culture.

The present invention provides an artificial basement membrane, composed of the Type I-Type IV collagen hybrid gel.

The present invention provides a method for producing a Type I-Type IV collagen hybrid gel, characterized in that: a hybrid collagen solution is produced by mixing 100 to 500 parts by mass of a Type I collagen solution, having fibrosis ability, with a concentration of 0.05 to 10 mg/ml, relative to 100 parts by mass of a Type IV collagen solution, having gelling ability, with a concentration of 0.05 to 10 mg/ml, at a temperature of 0 to 4° C.; the hybrid collagen solution is adjusted osmotic pressure from 0.5 to 2 times of human body fluid and neutral at a temperature of 0 to 4° C.; and then a three-dimensional gel is formed by incubation at a temperature of 30 to 40° C. for 10 minutes to 2 hours, under $CO_2$ condition.

The present invention provides the method for producing the Type I-Type IV collagen hybrid gel, characterized in that incubation is carried out at a temperature of 30 to 40° C. for 1 to 24 hours, by further adding the laminin to the three-dimensional gel, so as to be a concentration of 10 to 200 µg/ml.

The present invention provides a method for producing a cell culture plate, characterized in that: a hybrid collagen solution is produced by mixing 100 to 500 parts by mass of a Type I collagen solution, having fibrosis ability, with a concentration of 0.05 to 10 mg/ml, relative to 100 parts by mass of a Type IV collagen solution, having gelling ability, with a concentration of 0.05 to 10 mg/ml, at a temperature of 0 to 4° C.; the hybrid collagen solution is adjusted osmotic pressure from 0.5 to 2 times of human body fluid and neutral at a temperature of 0 to 4° C.; and then a three-dimensional gel is formed by putting the resultant solution on a support for cell culture plate and incubating at a temperature of 30 to 40° C. for 10 minutes to 2 hours, under $CO_2$ condition.

The present invention provides the method for producing the cell culture plate, characterized in that incubation is carried out at a temperature of 30 to 40° C. for 1 to 24 hours, by further adding the laminin to the three-dimensional gel, so as to be a concentration of 10 to 200 µg/ml, subsequent to formation of the three-dimensional gel.

The present invention provides a method for producing an artificial basement membrane, characterized in that: a hybrid collagen solution is produced by mixing 100 to 500 parts by mass of a Type I collagen solution, having fibrosis ability, with a concentration of 0.05 to 10 mg/ml, relative to 100 parts by mass of a Type IV collagen solution, having gelling ability, with a concentration of 0.05 to 10 mg/ml, at a temperature of 0 to 4° C.; the hybrid collagen solution is adjusted osmotic pressure from 0.5 to 2 times of human body fluid and neutral at a temperature of 0 to 4° C.; a three-dimensional gel is formed by coating the resultant solution on a flat plate and incubating at a temperature of 30 to 40° C. for 10 minutes to 2 hours, under $CO_2$ condition, so as to be a thickness of 0.01 to 3 mm; and then the three-dimensional gel is recovered from the flat plate.

The present invention provides the method for producing the artificial basement membrane, characterized in that incubation is carried out at a temperature of 30 to 40° C. for 1 to 24 hours, by adding laminin to the three-dimensional gel, so as to be a concentration of 10 to 200 µg/ml, subsequent to formation of the three-dimensional gel.

Effect of the Invention

According to the Type I-Type IV collagen hybrid gel of the present invention, a hybrid gel can be provided, which reduces use amount of the Type IV collagen giving small yield, is superior in gel strength, and has characteristics of the Type IV collagen, by mixing the Type IV collagen having gelling ability and the Type I collagen having fibrosis ability.

According to the present invention, the three-dimensional structure, where the membrane-like Type IV collagen is bound to the fibrous Type I collagen, can be formed in a short period of time, by incubating the Type I-Type IV collagen hybrid gel by a predetermined method.

According to the present invention, the three-dimensional structure, where the membrane-like Type IV collagen is bound to the fibrous Type I collagen, can be formed, by incubating the Type I-Type IV collagen hybrid gel by a predetermined method, and the cell culture plate, which further approximates to the basement membrane of a living body, can be produced by coating this hybrid gel onto the cell culture plate.

BRIEF DESCRIPTION OF THE DRAWINGS

FIG. 3A, FIG. 3B and FIG. 3C show results of Example 2, Comparative Example 1 and Comparative Example 2, respectively.

FIG. 4 is a transmission electron microscope photo showing results of Example 4, wherein FIG. 4A and FIG. 4B are transmission electron microscope photos of the Type IV collagen gel and the Type I-Type IV collagen hybrid gel, by a freeze-fracturing method, respectively.

FIG. 7A shows the colony of the ES cell on the Type I collagen gel of Comparative Example 1; FIG. 7B shows the colony of the ES cell on the hybrid gel between Type I-Type IV having gelling ability of Example 2; FIG.

DETAILED DESCRIPTION OF THE INVENTION

Figure 1:
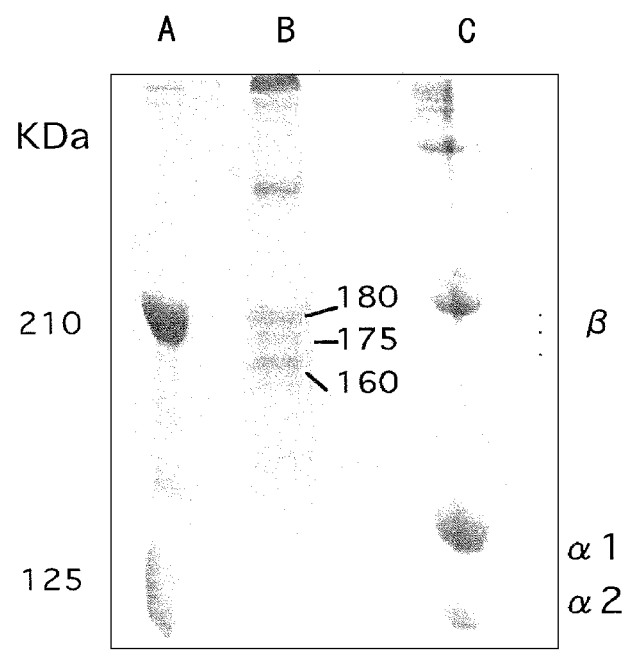
FIG. 1 is a drawing showing results of SDS-PAGE, wherein A represents a molecular weight marker; C is results of SDS-PAGE of the Type I collagen having fibrosis ability obtained in Production Example 1; and B is results of SDS-PAGE of the Type IV collagen having gelling ability obtained in Production Example 2.

The first aspect of the present invention is the Type I-Type IV collagen hybrid gel composed by mixing 100 to 500 parts by mass of a Type I collagen having fibrosis ability, based on 100 parts by mass of a Type IV collagen having gelling ability.

To provide cell culture environment by the basement membrane, use of the Type IV collagen, which is a main component of the basement membrane, is preferable, however, the Type IV collagen has small supply amount and has weak gelling ability. According to the present invention, the hybrid collagen can be provided, which is superior in gel strength while maintaining characteristics of the Type IV collagen as it is, by mixing the Type I collagen to small amount of the Type IV collagen. It should be noted that, as shown in Examples to be described later, to exert characteristics of the Type IV collagen, it is necessary for the Type IV collagen to form the network structure in the hybrid gel. Conventionally, there has not been known at all the mixing of the Type IV collagen and the Type I collagen, or a method for forming the three-dimensional gel from the resultant hybrid gel, and further the fact that such a hybrid gel can maintain characteristics of the Type IV collagen, which is a main component of the basement membrane. In the present invention, a hybrid gel is provided, which is obtained by using the Type IV collagen having gelling ability as the Type IV collagen, and using the Type I collagen having fibrosis ability as the Type I collagen, and by mixing 100 to 500 parts by mass, more preferably 100 to 400 parts by mass, and particularly preferably 100 to 300 parts by mass of the Type I collagen, based on 100 parts by mass of the Type IV collagen. It has been clarified that this hybrid gel can form the three-dimensional gel simply and conveniently under predetermined condition, and the three-dimensional gel obtained in this way has gel strength of the Type I collagen, while maintaining physiological function of the Type IV collagen as it is. Explanation will be given below in detail on the present invention.

(1) Type I Collagen Having Fibrosis Ability

In the present specification, "collagen" is a kind of a protein, and a general name of one, where three polypeptide chains are wound in a triple helix, and a collagen molecule may be composed of one kind of an α-chain, or may be composed of a multiple kinds of the α-chains coded by separate genes. The α-chain is usually called by being attached with a number after α, such as α1, α2 and α3, and further may be called by being attached with a collagen type, such as α1 (I). In the present invention, it may be a trimer of a combination, which is not present in nature, other than the Type I collagen present in nature such as, for example, [α1 (I)$_2$ α2 (I)], as long as it has fibrosis ability.

The Type I collagen to be used in the present invention is characterized by having fibrosis ability. The reason is because it has been clarified that characteristics of a component of the basement membrane of the Type IV collagen is exerted by binding membrane likely the Type IV collagen to the fibrous Type I collagen. It should be noted that, as for judgment on whether the Type I collagen to be used has fibrosis ability or not, the case where gel-like reproduced fiber having white turbidity with naked eyes is formed by an association structure can be confirmed as having fibrosis ability, when the Type I collagen to be used with a concentration of 0.1% is warmed to 37° C. in a sodium chloride-containing neutral buffer (a 0.9% NaCl-containing neutral buffer solution), under a condition of pH 7.6.

In general, the Type I collagen is contained in a large quantity in the connective tissue of an animal, however, when it is extracted by heat treatment, the specific three helical structure is destructed by thermal denaturation of the collagen to become a gelatin state. The present invention is characterized by using the Type I collagen having a three helical structure and fibrosis ability. As an extraction method for such a Type I collagen, there are included (1) a method for using an acidic solution, (2) a treatment method with an enzyme and (3) a method for solbulization by alkali treatment and the like, using bone or skin of an animal as a material.

(i) Treatment Method with an Acidic Solution

As an extraction raw material of the Type I collagen, there can be exemplified dermis or tendon of bovine, pig, chicken, ostrich, horse, fishes or the like. It is preferable to use a tissue of a young animal such as derived from a fetus, because yield is enhanced, however, it is not especially limited to the above, as long as the Type I collagen having fibrosis ability can be extracted.

For example, in the case of using the dermis of bovine, it is washed well using a phosphoric acid buffer solution, or a tris buffer solution (pH is 7.6), in which a proteolytic enzyme inhibitor is added with but sodium chloride is not contained. As the other method, a cows kin can be used, which is neutralized and washed with hydrochloric acid after depilation treatment by soaking in lime.

The cowskin after the pretreatment is cut into thin strips of about 1 cm square, and 0.5 M acetic acid is added in an amount of 10 times, based on the tissue weight, and stirred slowly at 40° C. or lower, more preferably 4 to 25° C. for 24 hours to 120 hours. After the extraction, the tissue remained undissolved is removed by centrifugal separation. By adding sodium chloride into the solution obtained by the centrifugal separation so that the final concentration becomes 2M, the Type I collagen is precipitated. Further, by re-dissolving the precipitate of the Type I collagen in 0.05 M acetic acid and adding sodium chloride so that the final concentration becomes 1M, and subjecting to centrifugal separation, precipitate of a crude Type I collagen is obtained. After that, by dissolving the precipitate in the tris hydrochloric acid buffer solution (pH is 7.6) and carrying out neutral salt differentiation, as needed, the Type I collagen can be purified further.

By the method for using the above acidic solution, a collagen can be obtained, which contains telopeptide, which is a non-helical region at the both ends of the three-helical region, and is in the same state as a collagen molecule present in a living body.

(ii) Enzyme Treatment

The cowskin after the pretreatment, which was obtained in the (i), is immersed in an acidic pepsin solution with hydrochloric acid of pH 2 to 3, and stirred slowly at all times at 40° C., which is shrinking temperature of the Type I collagen, or lower, more preferably 4 to 25° C., for 24 hours to 120 hours. An insoluble collagen is treated in an enzymatic way with pepsin, to dissolve the insoluble collagen.

Next, by adding a 0.005 N hydrochloric acid solution and stirring at 37° C., which is denaturation temperature of the Type I collagen, or lower, more preferably 20 to 25° C., for 12 hours to 60 hours, the Type I collagen is dissolved. As the acidic solution, acetic acid, hydrochloric acid, sulfuric acid, phosphoric acid, citric acid, and the other organic acids can be used suitably.

By filtering this solution and neutralizing the filtrate with an alkali such as sodium hydroxide to pH 6 to 8, pepsin is inactivated. After that, the solution is returned to an acidic state again, and two moles of sodium chloride is added to precipitate the collagen. After that, by similar operation as in the (i) a treatment method with an acidic solution, the crude Type I collagen or the purified Type I collagen can be obtained.

(iii) Treatment Method with an Alkali Solution

The cowskin after the pretreatment, which was obtained in the (i), is treated with an alkaline solution containing sodium sulfate such as a 5% sodium hydroxide solution containing 15% (w/v) sodium sulfate. In this way, a collagen maintaining the three-helical structure can be extracted. The alkali treatment method is superior in view of high extraction efficiency.

The Type I collagen binds to telopeptide composed of several tens residual groups of amino acid not taking a helical structure, at both ends of a collagen helical region, and the collagen, in which telopeptide portion was removed, is called atelocollagen. According to the above (ii) a treatment method with an enzyme, the Type I collagen can be obtained as atelocollagen. The Type I collagen to be used in the present invention may be atelocollagen, in which telopeptide was removed, as long as it can maintain the three-helical structure, and has fibrosis ability.

It should be noted that the above extraction method is one example, and one extracted by a modified method thereof or other methods may be used. Further, a commercial product may be used as well, as long as it is the Type I collagen having fibrosis ability.

(2) Type IV Collagen Having Gelling Ability

In the present specification, "the Type IV collagen" is a major collagen composing the basement membrane, and the molecule is composed of four domains of 7S, NC2, TH2 and NC1, and is a collagen forming a network by polymerization of four molecules at the 7S of the N terminal and by polymerization of two molecules at the NC1 of the C terminal, or a molecule equivalent in view of function thereof. The molecule equivalent in view of function of the Type IV collagen can be identified, for example, by an enzyme antibody method or an EIA method.

The Type IV collagen to be used in the present invention is characterized by having gelling ability. By gelling ability, the Type IV collagen can be bound in membrane state on a fibrous structure of the Type I collagen. As shown in Examples to be described later, use of the Type IV collagen not having gelling ability cannot form the Type IV collagen in membrane state on a fibrous structure of the Type I collagen, and also cannot exert characteristics as the Type IV collagen.

It should be noted that as for judgment on whether the Type IV collagen to be used has gelling ability or not, the case where the solution loses fluidity by association of the Type IV collagen after the Type IV collagen solution with a concentration of 1 mg/ml is stood still at 4° C. for 5 days, in a sodium chloride-containing neutral buffer (a 0.9% NaCl-containing neutral buffer solution), under a condition of pH 7.6, is confirmed to have gelling ability.

Such a Type IV collagen having gelling ability can be extracted using an acidic solution.

Firstly, as an extraction raw material of the Type IV collagen, there can be exemplified an eyeball lens capsule or placenta of bovine, pig, horse or the like. In particular, use of the eyeball lens capsule is preferable, because of high recovery rate and purity. However, it should not be limited to the above mentioned method, as long as the Type IV collagen can be extracted.

An extraction treatment method is given below.

For example, in the case of using the eyeball lens capsule of a frozen bovine, after thawing, firstly as the washing step, the eyeball lens capsule is washed with a 20 mM sodium phosphate solution with pH 7.2, containing a mixed solution of a protease inhibitor composed of 5 mM EDTA, 1 mM N-ethylmaleimide and 0.1 mM phenylmethylsulfonyl fluoride. Subsequently, the extraction step follows. Based on 1 g of the eyeball lens capsule, 5 to 10 ml of 1 mM hydrochloric acid is added to homogenize and stand still at 4° C. for 2 to 3 days. After centrifugal separation, the supernatant is stored at 4° C. The supernatant is dialyzed with 0.5 M acetic acid to remove the inhibitor, and by subsequent freeze drying, the Type IV collagen can be obtained.

It should be noted that, as shown in Examples to be described later, a band derived from the α-chain is present in the Type IV collagen extracted from the eyeball lens capsule. In the case where impurities, not derived from a collagen with 100 kDa or less, are contained, by purification with an ion exchange resin such as DEAE sepharose, the Type IV collagen with high purity can be obtained.

The Type IV collagen has four domains of 7S, NC2, TH2 and NC1, and the molecular N terminal and the molecular C terminal have the 7S region containing many cysteine residual groups, and a non-collagen helical region (the NC1 region), respectively, and the 7S region and the NC1 region have important role in forming a basement membrane structure by interaction of collagen molecules. In the present invention, it is not necessary to have all of the four domains, 7S, NC2, TH2 and NC1, as long as it has gelling ability.

It should be noted that the above extraction method is one example, and one extracted by a modified method thereof or other methods may be used. Further, a commercial product can be used as well, as long as it is the Type IV collagen having gelling ability.

(3) Laminin

Laminin is a constituent of the basement membrane. Laminin is a hetero trimer molecule, where three subunit chains called α, β and γ associated, and there are present 11 kinds of subunits in total, α1 to α5 in the α-chain, β1 to β3 in the β chain, and γ1 to γ3 in the γ chain, whose name is called by composition of the subunit chains. For example, laminin, where subunit α is α1, subunit β is β1 and subunit γ is γ1, is named laminin 111; and laminin, where subunit α is α2, subunit β is β1 and subunit γ is γ1, is named laminin 211. Theoretically, there may be 45 kinds of laminins by combination of the subunits. Laminin which can be used in the present invention can include other laminins to be found in the future, in addition to the following 15 kinds known at this time: laminin 111, 211, 121, 221, 332, 311, 321, 411, 421, 511, 521, 213, 423, 523 and 333. Further, it may be recombinant laminin other than purified products from an organ and cell secretion.

The Type IV collagen is present universally in the basement membrane, however, a composition subunit chain of laminin differs depending on a stage of organ development. The Type IV collagen takes a role of cell control specific to the basement membrane common among cells, as a basement membrane component, and laminin is possible to take charge of controlling delicate cell function, which is characteristic to the stage of organ development. For example, laminin is considered to control differentiation and growth of a cell by binding with integrin, dystroglycan, syndecan, which are cell receptors. Therefore, by binding various laminins to the Type I-Type IV collagen hybrid gel, differentiation or growth of a cultured cell can be controlled.

(4) Type I-Type IV Collagen Hybrid Gel

The Type I-Type IV collagen hybrid gel of the present invention is made by mixing 100 to 500 parts by mass of the Type I collagen having fibrosis ability, based on 100 parts by mass of the Type IV collagen having gelling ability. As described above, the hybrid gel blended in the above range can form the three-dimensional gel, in which a membrane-like substance by the Type IV collagen binds to the fibrous structure by the Type I collagen, under predetermined condition, and the resultant three-dimensional gel obtained in this way has gel strength of the Type I collagen, while maintaining physiological function of the Type IV collagen as it is.

Conventionally, the Type I collagen has been utilized as a substrate of three-dimensional cell culture, however, the Type I collagen does not have characteristics of the basement membrane, and thus cannot be said optimal for culture of the ES cell required in regenerative medicine or the like. Therefore, it is necessary to compose the three-dimensional gel, which maintains physiological function of the basement membrane and is stable, for maintaining culture of the ES cell or a cell differentiation-introduced therefrom, and further, for culture or growth of the tissue stem cell separated from various organs. The Type I-Type IV collagen hybrid gel of the present invention is superior in gel strength, and can maintain characteristics of the Type IV collagen, and provide cell culture environment approximate to the basement membrane of a living body.

In addition, the Type I-Type IV collagen hybrid gel of the present invention can bind other basement membrane components such as laminin. In the basement membrane of a living body, the network structure of the Type IV collagen and the laminin are bound in a complex way to form a stereo structure of the basement membrane. By further binding the laminin to the Type I-Type IV collagen hybrid gel of the present invention, cell culture environment more approximate to the basement membrane can be provided. Binding amount of laminin is a concentration of 10 to 200 μg/ml, and more preferably 20 to 150 μg/ml, to the Type I-Type IV collagen hybrid gel. It should be noted that kind of laminin to be bound is not especially limited, and it can be bound by selecting from various laminins corresponding to an object thereof.

It should be noted that the Type I-Type IV collagen hybrid gel of the present invention is a water-containing gel. Blending ratio of the Type I collagen and the Type IV collagen is the above range, however, total concentration of the Type I collagen and the Type IV collagen contained in the hybrid gel is 0.05 to 10 mg/ml, more preferably 0.1 to 8 mg/ml, and particularly preferably 0.1 to 6 mg/ml. This range can secure gel strength approximate to the basement membrane, and exert characteristics of the Type IV collagen.

On the other hand, the Type I-Type IV collagen hybrid gel of the present invention may be dried and frozen, after forming the three-dimensional gel. In this way, high degree of storage property can be secured. It should be noted that, by subsequent addition of a culture solution or the like, the three-dimensional gel can be formed again.

(5) Production Method for the Three-Dimension Gel by the Type I-Type IV Collagen Hybrid Gel The Type I-Type IV collagen hybrid gel of the present invention uses the Type I collagen and the Type IV collagen having different association temperature, however, it has been clarified that the three-dimension gel can be formed by a simple and convenient method. A method for forming the three-dimension gel from the Type I-Type IV collagen hybrid gel of the present invention is not especially limited, and the following method can be used suitably. That is, The hybrid collagen solution is produced by mixing 100 to 500 parts by mass of the Type I collagen solution, having fibrosis ability, with a concentration of 0.05 to 10 mg/ml, based on 100 parts by mass of the Type IV collagen solution, having gelling ability, with a concentration of 0.05 to 10 mg/ml, at a temperature of 0 to 4° C.; the hybrid collagen solution is adjusted osmotic pressure from 0.5 to 2 times of human body fluid and neutral by adding an elctrolyte-containing neutral buffer such as a sodium chloride-containing neutral buffer solution to the hybrid collagen solution, so as to be a sodium chloride concentration of 0.5 to 2% by mass, preferably 0.7 to 1.5% by mass, more preferably 0.9% by mass at a temperature of 0 to 4° C.; and then it is incubated at a temperature of 30 to 40° C. for 10 minutes to 2 hours, under $CO_2$ condition. In this way the three-dimension gel can be formed.

(i) Solution of the Type IV Collagen

Concentration of the solution of the Type IV collagen to be used in the present invention is 0.05 to 10 mg/ml, and more preferably 0.1 to 5 mg/ml. As dissolved solution of the Type IV collagen, it may be enough to use a solution which can dissolve these, in consideration of isoelectric point or the like of the Type IV collagen to be used. For example, in the case of using the Type IV collagen with the isoelectric point of 7.0 to 9.5, it can be used by dissolving in an acidic solution with pH 2 to 4, and more preferably pH 3 to 4, because of having superior solubility and less denaturation. As such an acidic solution, there can be exemplified 2 to 80 mM, and more preferably 5 to 50 mM acetic acid solution, and 0.5 to 20 mM, and more preferably 1 to 10 mM hydrochloric acid solution.

(ii) Solution of the Type I Collagen

Concentration of the solution of the Type I collagen to be used in the present invention is 0.05 to 10 mg/ml, and more preferably 0.1 to 5 mg/ml. As dissolved solution of the Type I collagen, similarly as the Type IV collagen, it may be enough to use a solution which can dissolve these, in consideration of isoelectric point or the like of the Type I collagen to be used. For example, in the case of using the Type I collagen with the isoelectric point of 7.0 to 9.5, it can be used by dissolving in an acidic solution with pH 2 to 4, and more preferably pH 3 to 4, because of having superior solubility and less denaturation. As such an acidic solution, there can be exemplified, similarly as the Type IV collagen, 2 to 80 mM, and more preferably 5 to 50 mM acetic acid solution, and 0.5 to 20 mM, and more preferably 1 to 10 mM hydrochloric acid solution. It is preferable that the Type I collagen solution is stored in an ice-cooling state.

(iii) Production of the Solution of the Hybrid Collagen

The hybrid collagen solution is obtained by mixing 100 to 500 parts by mass of the Type I collagen solution with a concentration of 0.05 to 10 mg/ml, based on 100 parts by mass of the Type IV collagen solution with a concentration of 0.05 to 10 mg/ml, at a temperature of 0 to 4° C., more preferably 0 to 3° C. and more preferably under ice-cooling condition. The temperature can mix both of the Type I collagen and the Type IV collagen without gelling. It should be noted that blending ratio of each collagen in the resultant Type I-Type IV collagen hybrid gel can be adjusted by selecting blending amount of the Type IV collagen solution and the Type I collagen solution. It is preferable that the Type IV collagen solution is stored under an ice-cooling condition.

(iv) Production of a Buffer Solution of the Hybrid Collagen

In the present invention, the hybrid collagen solution is adjusted osmotic pressure from 0.5 to 2 times of human body fluid, preferably 0.7 to 1.5 times, more preferably isotonic to human body fluid and neutral, at a temperature of 0 to 4° C., more preferably 0 to 3° C., and more preferably under an ice-cooling condition. Specifically, an electrolyte neutral buffer such as a sodium chloride-containing neutral buffer solution is added to the hybrid collagen solution, so as to be a sodium chloride concentration of 0.5 to 2% by mass, preferably 0.7 to 1.5% by mass, more preferably 0.9% by mass at a temperature of 0 to 4° C.

It should be noted that, as the neutral buffer solution to be used to produce the neutral buffer solution containing sodium chloride, there is a buffer solution with pH 6 to 8, more preferably pH 7 to 8, and most preferably pH 7.6, and for example, a phosphoric acid buffer solution or a tris buffer solution can be used. In addition, concentration of sodium chloride should be 5 to 20 times 0.9% by mass, which is salt concentration of a normal saline solution, and more preferably 7 to 15 times salt concentration. For example, in the case of using the neutral buffer solution containing sodium chloride in a concentration of 9% by mass, by using 1/10 thereof, the concentration can be adjusted to from 0.5 to 2% by mass, preferably 0.7 to 1.5% by mass, more preferably 0.9% by mass simply and conveniently. Incidentally, a salt such as potassium chloride can be used for adjusting the osmotic pressure of the hybrid collagen solution, provided that the solution is adjusted so as to have osmotic pressure from 0.5 to 2 times of human body fluid.

As a method for forming the fibrous structure from the Type I collagen, there has been known, as described in the NON-PATENT LITERATURE 4, an incubation method at 37° C. for 6 hours under 5% $CO_2$ condition, by adding DMEM having three-times concentration of sodium hydrogen carbonate or the like into a hydrochloric acid solution of the Type I collage. However, it has not been known at all that the three-dimensional gel is formed by mixing the Type I collagen and the Type IV collagen. In the present invention, by adding a neutral buffer such as a neutral buffer solution with the sodium chloride concentration to the hybrid collagen solution at a temperature of 0 to 4° C. so as to adjust osmotic pressure from 0.5 to 2 times of human body fluid, each collagen is mixed uniformly while preventing gelling of both of the Type I collagen and the Type IV collagen.

(v) Three-Dimension Gelling

The hybrid collagen buffer solution is incubated at a temperature of 30 to 40° C., and more preferably 35 to 37° C., for 10 minutes to 2 hours, and more preferably for 30 to 60 minutes. It has been clarified that this step provides association and gelling of the Type IV collagen, which did not associate conventionally unless at 4° C., by co-presence of the Type I collagen. That is, it is possible to make gelling of the Type I collagen and the Type IV collagen simultaneously, at 37° C., which is fiber forming temperature of the Type I collagen. Furthermore, a conventional method required such a long period of time as five days for making the Type IV collagen gelled, however, according to the present invention, the gelling is possible in such an extremely short period of time as within two hours. Furthermore, the three-dimensional structure thereof is one, where a membrane-like substance by the Type IV collagen is formed at the fibrous structure by the Type I collagen, and is similar to the network structure of the Type IV collagen present in the basement membrane. As a result, the hybrid gel of the present invention can maintain well characteristics of the Type IV collagen present in the basement membrane.

(vi) Addition of Laminin

Into the Type I-Type IV collagen hybrid gel of the present invention, laminin, which is a basement membrane composition, can be added, and in this way, the hybrid gel more approximate to the basement membrane can be produced.

A method for binding the laminin is not especially limited, however, preferably, incubation is carried out at a temperature of 30 to 40° C. for 1 to 24 hours, by adding laminin to the three-dimensional gel, so as to be a concentration of 10 to 200 µg/ml, after forming the three-dimensional gel. In the basement membrane, laminin also forms an associated body, however, it has not been clear whether laminin binds or not, in the three-dimensional gel composed of the Type I collagen and the Type IV collagen. In the present invention, it has been found that laminin can be bound to the Type I-Type IV collagen hybrid gel, not by mixing a laminin solution to a solution of the hybrid collagen, but by once forming the three-dimensional gel and then adding the laminin solution thereto to incubate this under the condition.

It should be noted that, because the Type I-Type IV collagen hybrid gel to add laminin constitutes the three-dimensional gel, it is not possible to stir this after adding laminin. However, by stratifing the laminin on the three-dimensional gel and incubating, the stratified laminin is bound to the gel and maintained. The Type I-Type IV collagen hybrid gel bound with laminin can be produced by washing the three-dimensional gel with a buffer solution or a cell culture solution, after incubation.

It is preferable to use laminin, as one dissolved in a phosphoric acid buffer solution, or a tris buffer solution or the like.

(6) Cell Culture Plate

A support composing the cell culture plate in the present invention widely includes one which is used in cell culture and can immobilize the Type I-Type IV collagen hybrid gel. Therefore, there is included also a chip, an array, a plate such as a micro-titer plate or a micro well plate, a Petri dish, slide glass, a film, beads or the like.

In addition, an immobilization method to the support may be a physical bonding in addition to a chemical bonding. As a material to be used as the support, for example, glass, a natural polymer and a synthetic polymer, a metal (including an alloy as well) can be exemplified, and it may be a composite body composed of two or more kinds thereof in combination.

As the polymer, there can be exemplified polyethylene, ethylene, polypropylene, polyisobutylene, polyethylene terephthalate, unsaturated polyester, fluorine-containing resin, polyvinyl chloride, polyvinylidene chloride, polyvinyl acetate, polyvinyl alcohol, polyvinyl acetal, acrylic resin, polyacrylonitrile, polystyrene, acetal resin, polycarbonate, polyamide, phenolic resin, urea resin, epoxy resin, melamine resin, styrene-acrylonitrile copolymer, acrylonitrile-butadiene-styrene copolymer, silicone resin, polyphenylene oxide, polysulfone, or the like.

In addition, in the present invention, a membrane used in blotting, such as a nitrocellulose membrane, a nylon membrane, a PVDF membrane can also be used.

The cell culture plate of the present invention is one, where the Type I-Type IV collagen hybrid gel is coated on the support for cell culture. Preferably it is one, where the hybrid gel forms the three-dimensional gel. It is because, by the three-dimensional gel, characteristics of the Type IV collagen is exerted and culture environment approximate to the basement membrane may be formed. It should be noted that the Type I-Type IV collagen hybrid gel is not necessarily coated at the whole surface of the support, and it is enough that the Type I-Type IV collagen hybrid gel is coated at least at the cell culture surface.

The cell culture plate of the present invention can be produced in accordance with a method for producing the three-dimensional gel from the Type I collagen and the Type IV collagen.

Specifically, a hybrid collagen solution is produced by mixing 100 to 500 parts by mass of a Type I collagen solution, having fibrosis ability, with a concentration of 0.05 to 10 mg/ml, based on 100 parts by mass of a Type IV collagen solution, having gelling ability, with a concentration of 0.05 to 10 mg/ml, at a temperature of 0 to 4° C.; the hybrid collagen solution is adjusted osmotic pressure from 0.5 to 2 times of human body fluid and neutral at a temperature of 0 to 4° C.; and incubation is carried out at a temperature of 30 to 40° C. for 10 minutes to 2 hours, under $CO_2$ condition by putting the resultant solution on the cell culture plate. It is characterized in that, in this way, the three-dimensional gel is formed.

Operation is carried out similarly as a production method for the three-dimensional gel by the Type I-Type IV collagen hybrid gel, up to production of the hybrid collagen buffer solution. Different point is that incubation is carried out at a temperature of 30 to 40° C. for 10 minutes to 2 hours, under $CO_2$ condition by putting the resultant solution on the cell culture plate. In this way, the three-dimensional gel can be formed on the cell culture plate.

It should be noted that, similarly, by carrying out incubation at a temperature of 30 to 40° C. for 1 to 24 hours, by adding laminin, so as to be a concentration of 10 to 200 μg/ml, to the three-dimensional gel, the three-dimensional gel composed of the Type I collagen bound with laminin and the Type. IV collagen can be produced on cell culture plate.

The stem cell can be cultured using the cell culture plate of the present invention. It should be noted that, the stem cell means a cell having multipotency (i.e. pluripotency). The stem cell usually can reproduce a tissue, when the tissue received damage. As the stem cell, there is included an embryonic stem (ES) cell, a tissue stem cell (it may also be called a systemicity stem cell, a tissue-specific stem cell or a somatic stem cell), a germ stem cell, an iPS cell or the like. The stem cell also includes an artificially prepared cell, for example, a fusion cell, a re-programmed cell, an artificial pluripotency stem cell, as long as it has self-reproducing ability and pluripotency.

(7) Artificial Basement Membrane

In the present invention, the artificial basement membrane can be produced by using the Type I-Type IV collagen hybrid gel. It should be noted that the artificial basement membrane is one imitating the basement membrane of a living body, and for example, the cell culture plate is a cell culture plate having the artificial basement membrane at the surface.

Such an artificial basement membrane can be produced in accordance with the above method for producing the three-dimensional gel from the Type I collagen and the Type IV collagen.

Specifically, a hybrid collagen solution is produced by mixing 100 to 500 parts by mass of a Type I collagen solution, having fibrosis ability, with a concentration of 0.05 to 10 mg/ml, based on 100 parts by mass of a Type IV collagen solution, having gelling ability, with a concentration of 0.05 to 10 mg/ml, at a temperature of 0 to 4° C.; the hybrid collagen solution is adjusted osmotic pressure from 0.5 to 2 times of human body fluid and neutral at a temperature of 0 to 4° C.; and by putting the resultant solution on a flat plate, incubation is carried out at a temperature of 30 to 40° C. for 10 minutes to 2 hours, under $CO_2$ condition. It is characterized in that, in this way, the three-dimensional gel is formed.

Operation is carried out similarly as a production method for the three-dimensional gel by the Type I-Type IV collagen hybrid gel, up to production of the hybrid collagen buffer solution. Different point is that incubation is carried out at a temperature of 30 to 40° C. for 10 minutes to 2 hours, under $Cd_2$ condition by putting the resultant solution on the flat plate, and the three-dimensional gel is recovered from the flat plate. In this way, an artificial basement membrane composed of only the three-dimensional gel can be produced.

It should be noted that, similarly, by carrying out incubation at a temperature of 30 to 40° C. for 1 to 24 hours, by adding the laminin, so as to be a concentration of 10 to 200 μg/ml, to the three-dimensional gel, the three-dimensional gel composed of the Type I collagen bound with laminin and the Type IV collagen can be produced on cell culture plate.

Type I-Type IV collagen hybrid gel of the present invention can form three-dimensional gel by simple and convenient operation, and the three-dimensional gel is one that maintains gel strength derived from Type I collagen, and maintains characteristics as a basement membrane component by Type IV collagen, and thus can provide culture environment approximate to environment of the basement membrane of a living body in low cost, by producing a cell culture plate using the same.

EXAMPLES

Explanation will be given next specifically on the present invention with reference to Examples, however, the present invention should not be limited to these Examples.

Production Example 1

A soluble protein was removed by washing a dermis of cow with a 5% saline solution. This cowskin was immersed in an aqueous solution of trypsin with pH 8, and stood still at 25° C. for 90 hours under stirring at all times. Next, the cowskin was washed with flowing water to remove the enzyme, immersed in an aqueous acidic solution of acetic acid with pH 2 to 3, and stirred at 20 to 25° C. for 24 hours to obtain a viscous solution. The Type I collagen extracted was purified by repeating salting-out under acidic and neutral conditions. Isoelectric point was pH 9.3.

This Type I collagen was adjusted to a concentration of 0.1%, and warmed to 37° C. in a sodium chloride-containing neutral buffer (a 0.9% NaCl-containing phosphoric acid buffer solution), under a condition of pH 7.6. A fibrous structure was formed by association due to the warming, to form gel-like reproduced fiber having white turbidity with naked eyes.

It should be noted that, when the resultant Type I collagen was subjected to SDS-PAGE with 5% polyacrylamide, presence of an α-chain composed of two different kinds of α1 and α2, and a β-chain of a dimer of the α-chain, was confirmed. Results are shown in C of FIG. 1.

Production Example 2

A eyeball lens capsule of cow was washed with 20 mM sodium phosphate buffer solution with pH 7.2, containing a mixed solution of a protease inhibitor composed of 5 mM EDTA, 1 mM N-ethylmaleimide and 0.1 mM phenylmethylsulfonyl fluoride. Subsequently, as the extraction step, 5 to 10 ml of 0.5 M acetic acid was added per 1 g of the eyeball lens capsule to homogenize, and stirred at 4° C. for 3 days. After centrifugal separation, the supernatant was stored at 4° C. The supernatant was dialyzed with 1 mM hydrochloric acid to remove the inhibitor, and to obtain a Type IV collagen. Isoelectric point was pH 8.7. It should be noted that the Type IV collagen was stored with freeze drying.

The Type IV collagen was adjusted to a concentration of 1 mg/ml in a sodium chloride-containing neutral buffer (a 0.9% NaCl-containing phosphoric acid buffer solution), under a condition of pH 7.6, and stood still at 4° C. for 5 days, resulting in association and gelling.

When the resultant Type IV collagen was subjected to SDS-PAGE with 5% polyacrylamide in a reduced state, a band derived from three α-chains of the Type IV collagen was observed at the vicinity of 160 to 180 kDa. Results are shown in B of FIG. 1.

Example 1

Production of the Type I-Type IV Collagen Hybrid Gel (1) A collagen hybrid gel was prepared, in accordance with the following protocol, from the Type I collagen obtained in Production Example 1 and the Type IV collagen obtained in Production Example 2.

Firstly, into 56 μl of ultra pure water ("Milli Q water", produced by Millipore Co., Ltd.) cooled on ice, 24 μl of PBS (−) with ten times concentration, containing 9% by mass of sodium chloride, 80 μl of 5 mM acetic acid solution (4.5 mg/ml) of the Type I collagen obtained in Production Example 1, and 80 μl of 5 mM acetic acid solution (1.5 mg/ml) of the Type IV collagen obtained in Production Example 2, were added in this order, and pH was confirmed to be 7.6.

(2) This solution was charged into an Eppendorf tube and incubated at 37° C. for 1 hour under 5% $CO_2$ condition and subjected to gelling.

Figure 2:
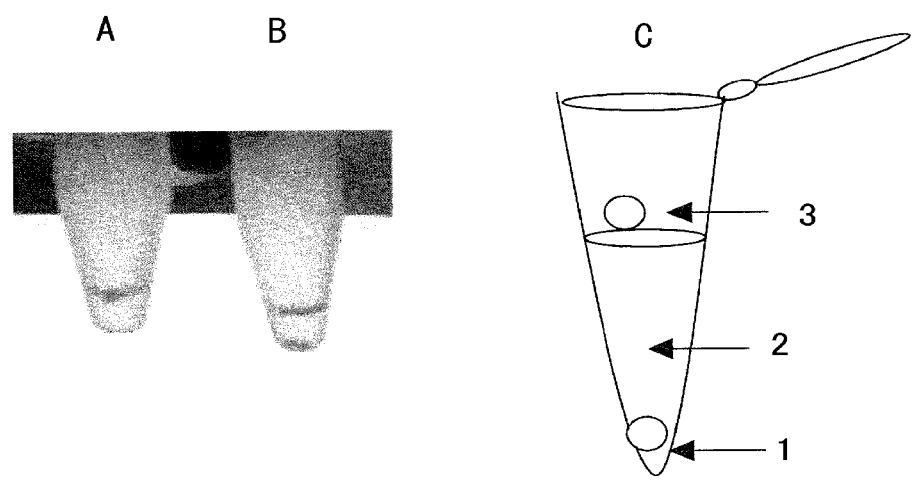
FIG. 2 is a drawing explaining an evaluation method for gel strength in the case where the three-dimensional gel was produced, wherein A represents an aspect, where beads are held onto the three-dimensional gel composed of the Type I collagen and the Type IV collagen obtained in Example 1, formed in an Eppendorf tube; B represents an aspect, where the beads fall on the bottom; and C is a schematic drawing thereof.

After that, zirconia beads were put gently on the gel, and observed them after 1 hour. Gel was formed and the beads were held on the upper surface of the gel, as shown in A of FIG. 2. It should be noted that, in the case of insufficient gel formation, the beads fall down to the lower surface, as shown in B of FIG. 2. It should be noted that C of FIG. 2 is a drawing showing this schematically.

Example 2

Production of the Type I-Type IV Collagen Mixture and a Well Plate (1) The Type I-Type IV collagen hybrid gel of the present invention was prepared, in accordance with the following protocol, from the Type I collagen obtained in Production Example 1 and the Type IV collagen obtained in Production Example 2.

(2) Firstly, into 56 μl of ultra pure water ("Milli Q water", produced by Millipore Co., Ltd.) cooled on ice, 24 μl of PBS (−) with ten times concentration, containing 9% by mass of sodium chloride, 80 μl of 5 mM acetic acid solution (4.5 mg/ml) of the Type I collagen obtained in Production Example 1, and 80 μl of 5 mM acetic acid solution (1.5 mg/ml) of the Type IV collagen obtained in Production Example 2, were added in this order, and pH was confirmed to be 7.6.

The solution was dispensed into a 96 well plate (trade name, 96 well cell culture plate, manufactured by Costar Co., Ltd.) in an amount of 50 μl/well. Then, this well plate was incubated at 37° C. for 1 hour under 5% $CO_2$ condition to produce a gel coating well plate, by making the solution gelled.

Comparative Example 1

Production of a Collagen Type I Gel and a Well Plate (1) The Type I collagen gel was prepared, in accordance with the following protocol, from the Type I collagen obtained in Production Example 1.

Firstly, into 136 μl of ultra pure water ("Milli Q water", produced by Millipore Co., Ltd.) cooled on ice, 24 μl of PBS (−) with ten times concentration, containing 9% by mass of sodium chloride, and 80 μl of 5 mM acetic acid solution (4.5 mg/ml) of the Type I collagen obtained in Production Example 1, were added on ice in this order. pH was confirmed to be 7.6.

(2) The solution was dispensed into a 96 well plate (trade name, 96 well cell culture plate, manufactured by Costar Co., Ltd.) in an amount of 50 μl/well. Then, this well plate was incubated at 37° C. for 1 hour under 5% $CO_2$ condition to produce a gel coating well plate, by making the solution gelled.

Comparative Example 2

Production of the Type IV Collagen-Type Hybrid Gel not having Type I Gelling Ability and a Well Plate (1) A hybrid collagen gel was prepared, in accordance with the following protocol, from the Type I collagen obtained in Production Example 1, and the Type IV collagen extracted using an enzyme. The bovine Type IV collagen extracted using an enzyme did not have gelling ability.

Firstly, into 112 µl of ultra pure water ("Milli Q water", produced by Millipore Co., Ltd.) cooled on ice, 24 µl of PBS (−) with ten times concentration, containing 9% by mass of sodium chloride, 80 µl of 5 mM acetic acid solution (4.5 mg/ml) of the Type I collagen obtained in Production Example 1, and 24 µl of 5 mM acetic acid solution (5 mg/ml) of the Type IV collagen extracted using an enzyme (the Type IV collagen not have gelling ability, extracted from a placenta using a pepsin enzyme according to the method of Sage et al. described in NON-PATENT LITERATURE 1: 5 mg/ml) were added on ice in this order and pH was confirmed to be 7.6.

(2) The solution was dispensed into a 96 well plate (trade name, 96 well cell culture plate, manufactured by Costar Co., Ltd.) in an amount of 50 µl/well. Then, this well plate was incubated at 37° C. for 1 hour, under 5% $CO_2$ condition to produce a gel coating well plate, by making the solution gelled.

Example 3

The well plates coated with the gel, prepared in Example 2, Comparative Example 1 and Comparative Example 2, were observed with a scanning electron microscope, after production by the following method.

(1) Onto the gel in each of the well plates, 50 µl of 2% glutaraldehyde was added and stood still at 4° C. for 2 hours.

(2) As the secondary immobilization, 1% osmium tetroxide was added and stood still at room temperature for 1 hour.

(3) The solution was stood still as follows: once in 100 µl/well of 50% ethanol for 10 minutes, once in 100 µl/well of 70% ethanol for 10 minutes, once in 100 µl/well of 80% ethanol for 10 minutes, twice in 100 µl/well of 90% ethanol for 10 minutes, twice in 100 µl/well of 95% ethanol for 10 minutes, and twice in 100 µl/well of 99.5% ethanol for 10 minutes, and then dehydration was carried out.

(4) Next, standing still was carried out twice in 100 µl/well of t-butyl alcohol for 10 minutes for replacement.

(5) After the replacement, freeze drying was carried out overnight.

Figure 3:
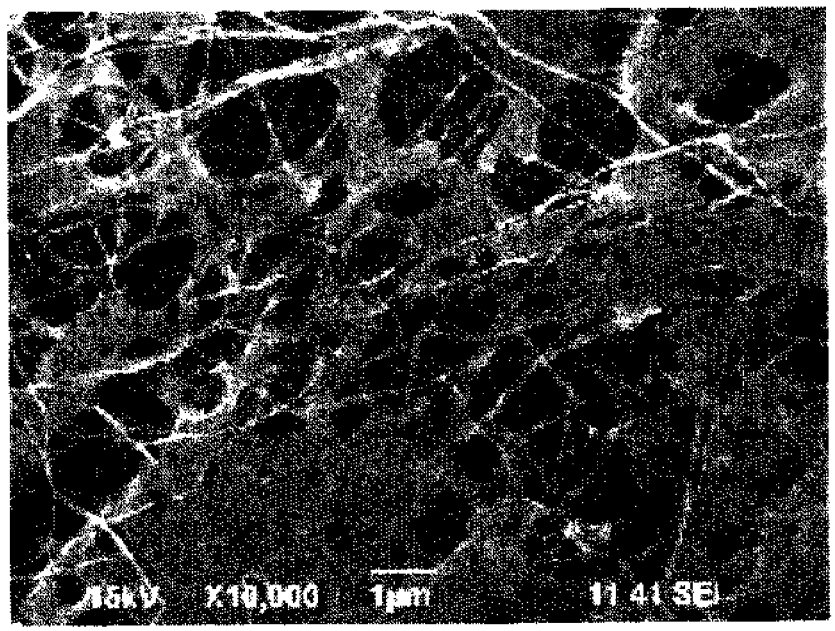
FIG. 3 is a scanning electron microscope photo of the gel coating well plates, prepared in Example 2, Comparative Example 1 and Comparative Example 2.
Figure 3:
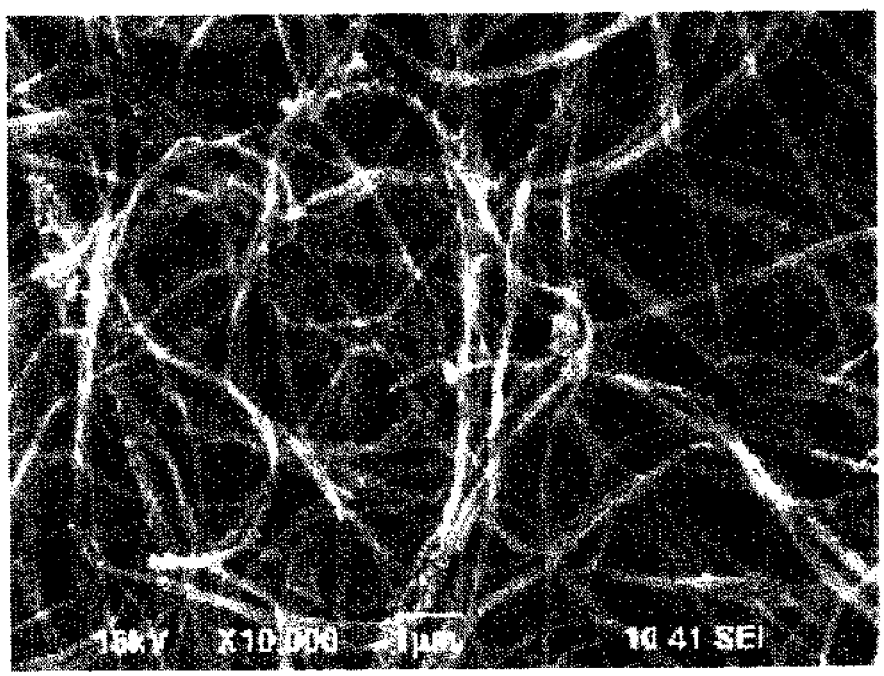
Figure 3C:
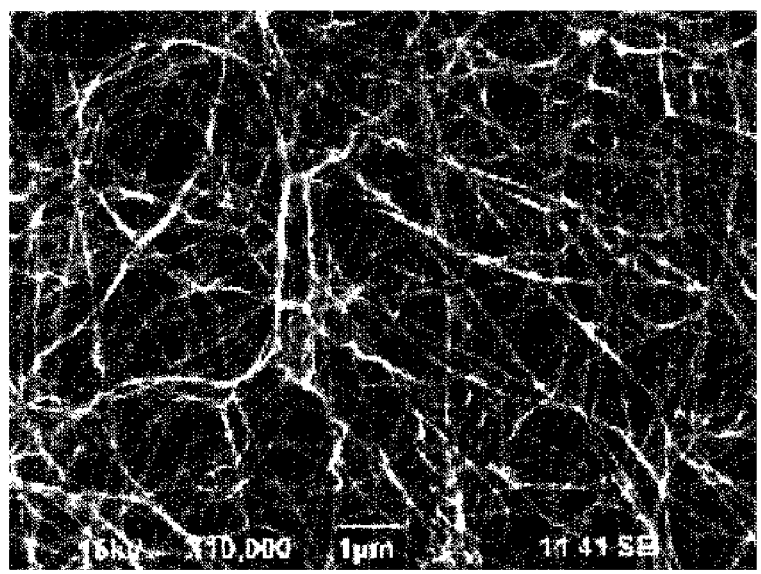

(6) After coating the freeze-dried sample with platinum for 20 seconds, it was observed with a scanning electron microscope (JCM-5700 (JEOL)) in conditions of 15 kV and a magnification of 10000 times. Results are shown in FIG. 3. The gel of Example 2, the gel of Comparative Example 1 and the gel of Comparative Example 2 are shown in FIG. 3A, FIG. 3B and FIG. 3C, respectively.

Example 4

The freeze-fracturing method was carried out on the Type IV collagen obtained in Production Example 2 and the Type I-Type IV collagen hybrid gel obtained in Example 2, to observe the fracture surfaces with a transmission electron microscope. FIG. 4A and FIG. 4B are transmission electron microscope photos of the Type IV collagen gel at 37° C. (magnification of 20000 times), and the Type I-Type IV collagen hybrid gel obtained in Example 2 (magnification of 5000 times), respectively.

(Results)

(1) As shown in FIGS. 3A, 3B and 3C, the Type I collagen is fibrous, and in each gel of Example 2, Comparative Example 1 and Comparative Example 2, a fibrous substance was observed. In each gel, it is supposed that a basic structure is constructed by the fibrous substance of the Type I collagen.

(2) As shown in FIG. 3A, in the Type I-Type IV collagen hybrid gel of the present invention of Example 2, a membrane-like constituent was observed along with the Type I collagen fiber. By comparison with FIG. 3B, it was clarified that the Type IV collagen having gelling ability is able to form the membrane-like substance between the Type I collagen fibers, by mixing with the Type I collagen having fibrosis ability.

(3) On the other hand, as shown in FIG. 3C, the gel of Comparative Example 2, which was obtained by adding the Type I collagen fiber and the Type IV collagen not having gelling ability, extracted with an enzyme, provides only the fibrous structure, and the membrane-like structure was not present. The Type IV collagen not having gelling ability has association ability different from one having gelling ability, and was thus not able to form the membrane-like substance by the Type IV collagen between the fibers composed of the Type I collagen.

(4) As shown in FIG. 4A, in the Type IV collagen, a uniform and fine structure of the associated body was observed also inside the gel, and as shown in FIG. 4B, in the Type I-Type IV collagen hybrid gel, a similar fine structure of the associated body was observed inside the gel.

Example 5

(1) Into the 5 mM acetic acid solution (1.5 mg/ml) of the Type I collagen obtained in Production Example 1, the 5 mM acetic acid solution of the Type IV collagen having gelling ability obtained in Production Example 2, was added in an amount of 0 mg/ml, 0.5 mg/ml and 1.0 mg/ml under cooling on ice.

(2) By operating similarly as in Example 1, sodium chloride concentration was made 0.9% by mass and neutral under ice cooling, and after that, incubation was carried out at 37° C. for 1 hour to make it gelled.

(3) After washing the resultant gel with PBS three times, a solution of laminin 111 or laminin 511 was added so as to be 50 µl/ml.

(4) Incubation was carried out at 37° C. for 2 hours, then washing was carried out with PBS three times for 20 minutes. After that, the gel was dissolved in a reducing buffer (containing mercaptoethanol) with a concentration of 2 times, and then SDS-PAGE was carried out to detect laminin bound to the gel using Western blot. Results are shown in FIG. 5A, FIG. 5B and FIG. 5C.

Figure 6:
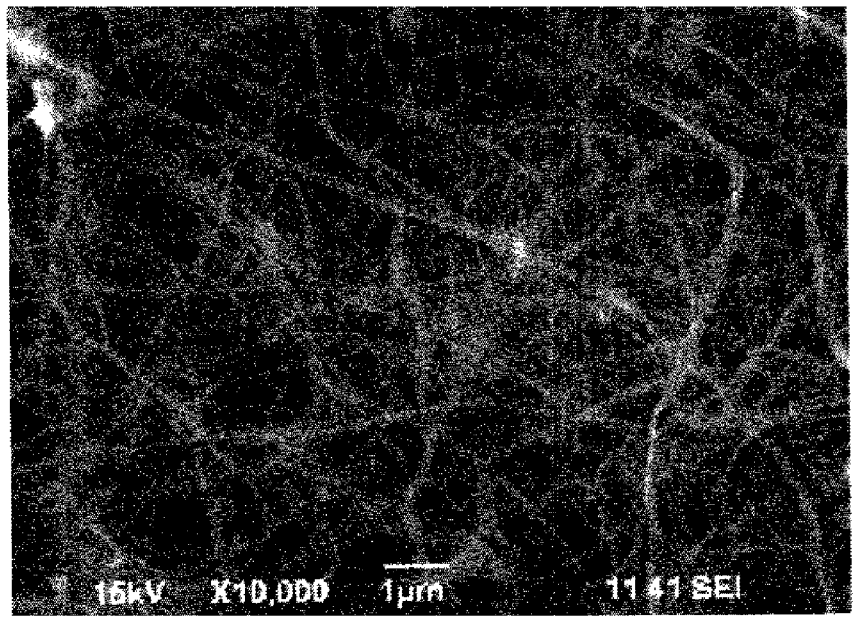
FIGS. 6A and 6B show scanning electron microscope photos of gel of Example 5.
Figure 6:
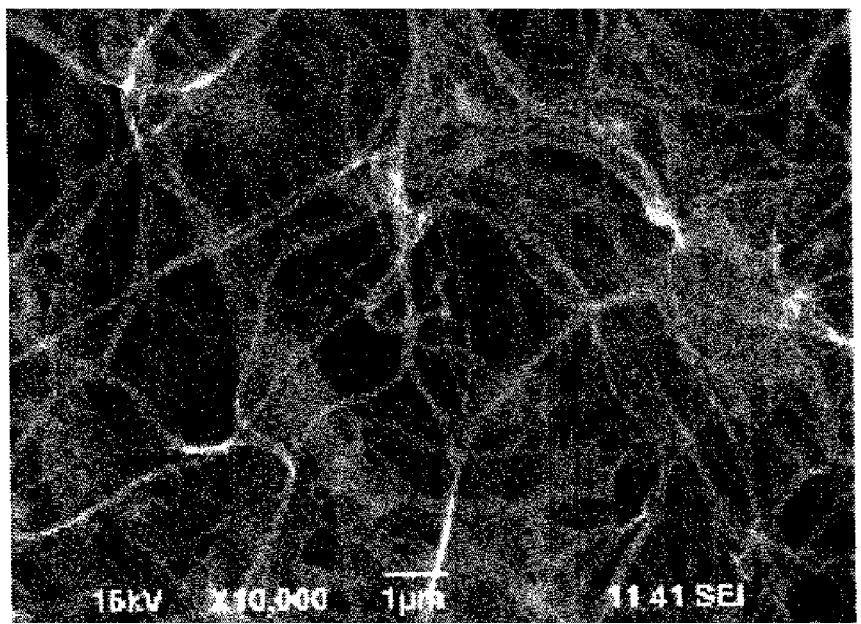

(5) Laminin 111 and laminin 511 were added to the hybrid gel mixed with 0.5 mg/ml of the Type IV collagen having gelling ability, and it was subjected to observation with a scanning electron microscope similarly as in Example 3 after immobilization by a similar method as in Example 3. Results are shown in FIG. 6.

Comparative Example 3

A gel was produced by similar operation as in Example 5, except that the 5 mM acetic acid solution (5 mg/ml) of the Type IV collagen extracted with an enzyme, not having gelling ability was added instead of the Type IV collagen having gelling ability obtained in Production Example 2, to carry out SDS-PAGE similarly as in Example 5. Results are shown in FIG. 5D.

(Results)

Figure 5:
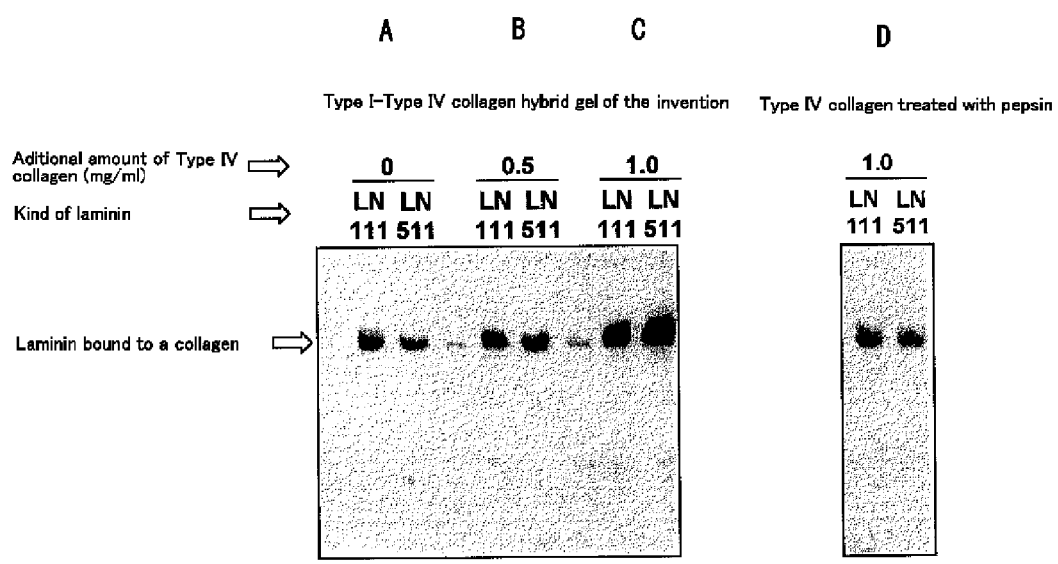
FIG. 5 A, B and C are drawings showing results of SDS-PAGE, wherein bonding amount of laminin to the Type I-Type IV collagen hybrid gels of the present invention, having different blending amount of the Type IV collagen, was evaluated, and D is a drawing showing results of SDS-PAGE in the case of using the Type IV collagen not having gelling ability.

(1) A of FIG. 5 is a gel, where 0 mg/ml of the Type IV collagen having gelling ability was added to the Type I collagen having fibrosis ability; B of FIG. 5 is a gel, where 0.5 mg/ml of the Type IV collagen having gelling ability was added to the Type I collagen; C of FIG. 5 is a gel, where 1.0 mg/ml of the Type IV collagen having gelling ability was added to the Type I collagen; and D of FIG. 5 is a gel, where 1.0 mg/ml of the Type IV collagen extracted with an enzyme, not having gelling ability was added to the Type I collagen.

As clarified from A to C of FIG. 5, in the hybrid gel between the Type I collagen and the Type IV collagen having gelling ability, binding amount of laminin increased in response to mixing amount of the Type IV collagen to the Type I collagen. Such an increase in bonding amount of laminin was observed similarly in both of laminin 111 and laminin 511.

(2) In comparing C of FIGS. 5 and D of FIG. 5, in the gel, where 1.0 mg/ml of the Type IV collagen not having gelling ability was added to the Type I collagen, binding amount thereof was low in both laminin 111 and laminin 511. From this result, it is clarified that the Type IV collagens obtained by different extraction methods differ in bonding amount of laminin, and it was inferred that laminin can be incorporated efficiently in the Type I-Type IV collagen hybrid gel, by using the Type IV collagen having gelling ability.

(3) FIG. 6A is one, in which laminin 111 was added to a hybrid gel, where 0.5 mg/ml of the Type IV collagen having gelling ability was mixed, and FIG. 6B is one, where laminin 511 was added. In both of FIG. 6A and FIG. 6B, formation of a membrane-like substance was observed between fibers by the addition of laminin. On the other hand, in FIG. 6A, a thin membrane structure is formed uniformly between fibers, while in FIG. 6B, the uniformity is lower as compared with FIG. 6A, and the membrane structure accompanying the Type I gel was different depending on kind of laminin added.

Example 6

(1) The Type I-Type IV collagen hybrid gel was produced by a similar method as in Example 2, to manufacture the gel coating well plate similarly as in Example 2.

(2) 10% bovine fetus serum, non-essential amino acid, penicillin and streptomycin, and sodium pyruvate were added to Glasgow minimum essential culture medium (produced by Gibco Co., Ltd.) to produce a culture medium.

An ES cell strain (ht7) was dispensed in an amount of $3.8 \times 10^3$ cells/"96 well", and cultured at 37° C. for 5 days, under 5% $CO_2$ condition to differentiate spontaneously.

The culture medium was replaced in a frequency of once a day, and also morphology of the cell was observed.

Figure 7:
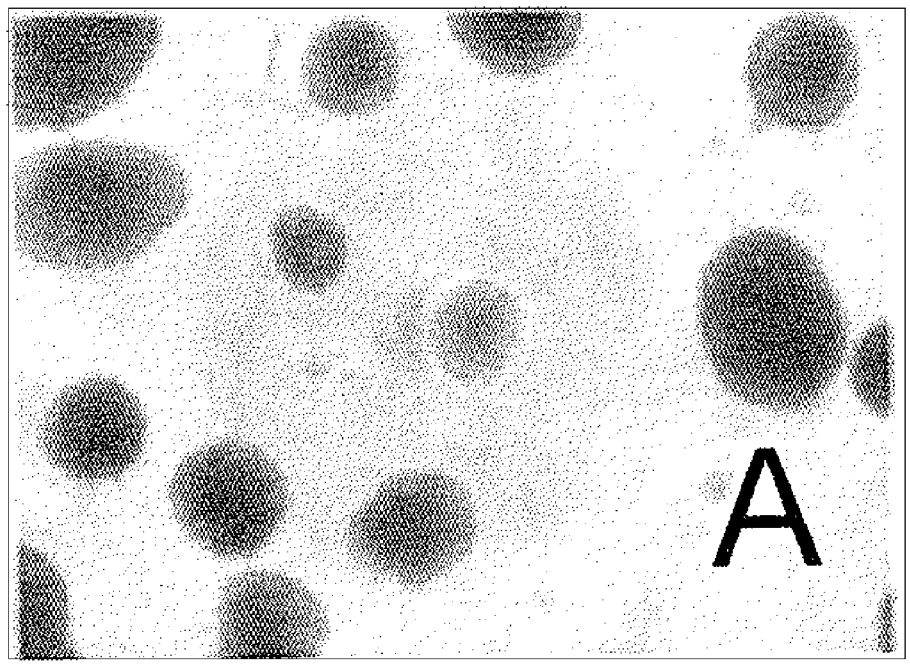
FIG. 7 is a drawing showing morphology of an ES cell colony, where the ES cell was cultured on the gel coating well plate produced using the Type I-Type IV collagen hybrid gel, which was formed in Example 6.
Figure 7:
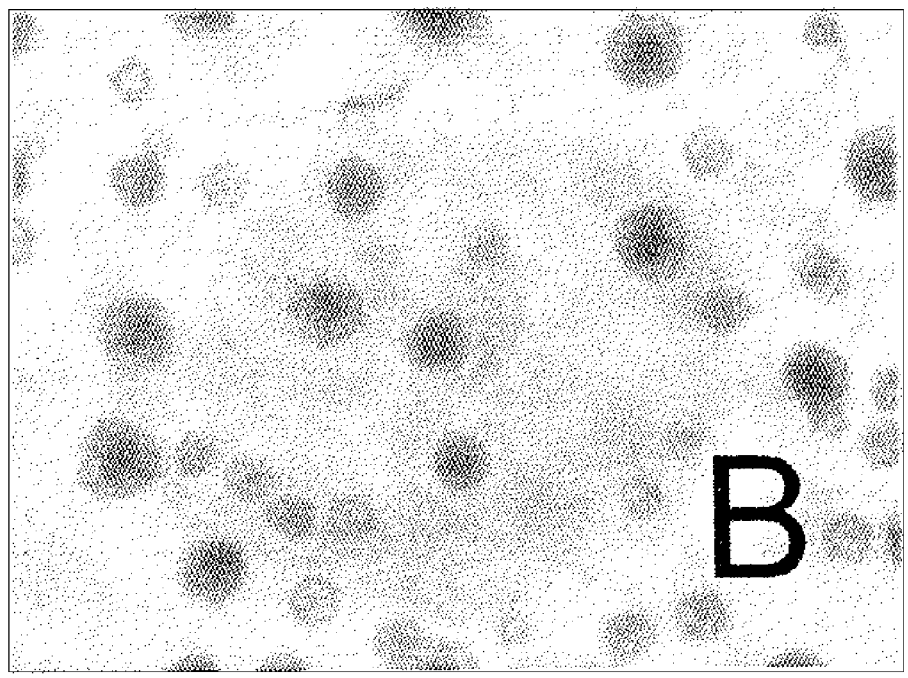
Figure 7C:
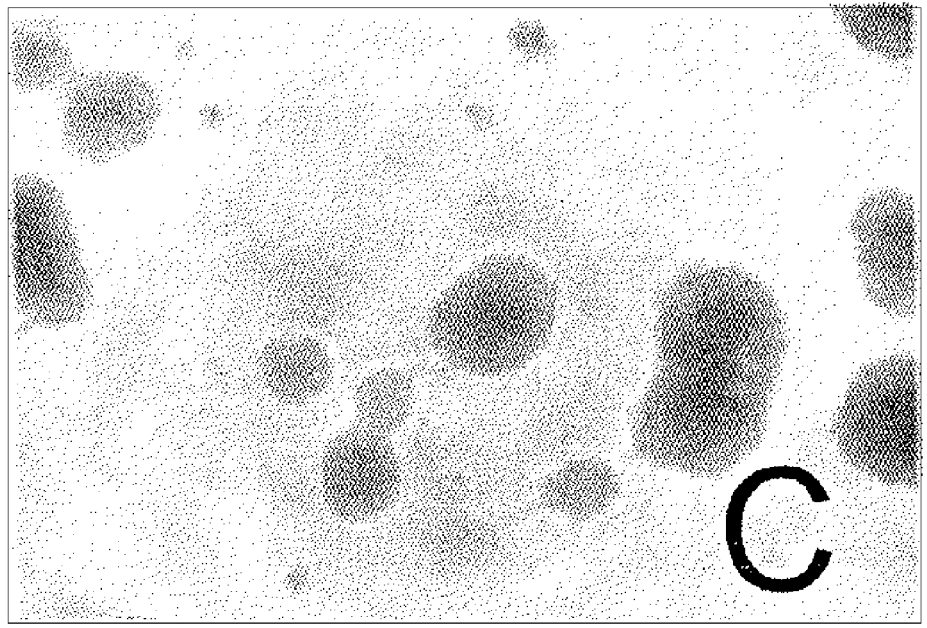
FIG. 7C shows the colony of the ES cell on the hybrid gel between Type I-Type IV extracted by an enzyme of Comparative Example 2.
Figure 7D:
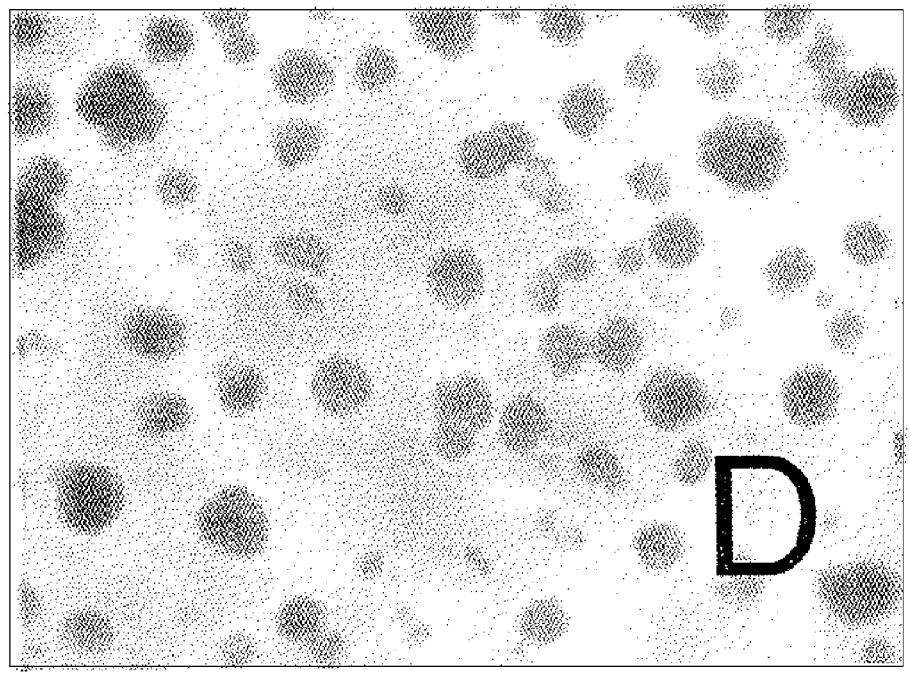
FIG. 7D shows the colony of the ES cell on the "Matrigel".

Morphology of an ES cell colony is shown in FIG. 7B. It should be noted that morphology of the ES cell colony was similarly observed, by similar operation as the above using the well plate produced in Comparative Example 1, the well plate produced in Comparative Example 2 and a commercial "Matrigel". Results are shown in FIG. 7A, FIG. 7C and FIG. 7D.

Figure 8:
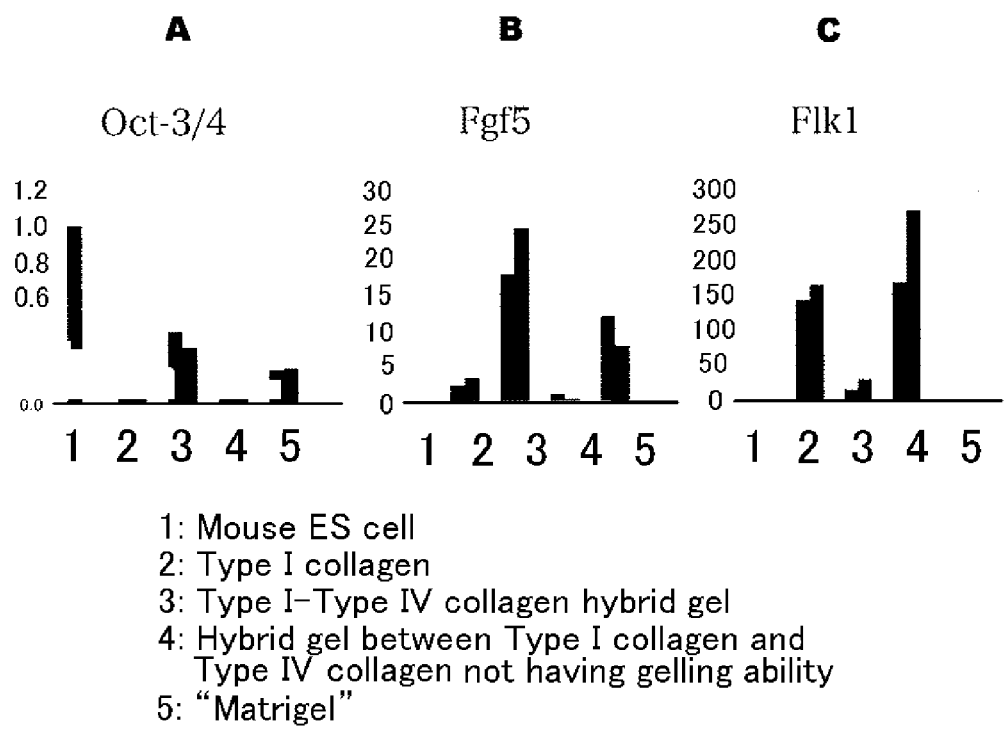
FIG. 8A, FIG. 8B, and FIG. 8C are drawings showing expressions of Oct-3/4, Fgf5 and Flk1, respectively.

In addition, whole RNA was extracted from a cell at five days of culture to examine expression of differentiation marker gene with a quantitative RT-PCR. A gene expression level is shown in FIG. 8.

Comparative Example 4

A well plate coated with a gel was produced by operating similarly as in Example 6, except that the Type I collagen gel of Comparative Example 1 and the hybrid gel between the Type I collagen and the Type IV collagen not having gelling ability of Comparative Example 2 were used instead of the Type I-Type IV collagen hybrid gel used in Example 6, to culture the mouse ES cell strain (ht7). In addition, a gel coating well plate was produced by adding the Matrigel™ (produced by Becton, Dickinson and Corp.) in an amount of 50 μl/well in a final concentration of 5 mg/ml, and gelling at 37° C. for 1 hour to culture the mouse ES cell strain (ht7).

Similarly as in Example 6, morphology of the ES cell colony and the gene expression level were observed on the mouse ES cell, along with the ES cell cultured by the above. Results are shown in FIG. 8.

(Results)

Morphology Observation of the Colony (1) FIG. 7A shows the ES cell colony in the Type I collagen gel of Comparative Example 1; FIG. 7B shows the ES cell colony in the hybrid gel between the Type I and the Type IV having gelling ability of Production Example 6; FIG. 7C shows the ES cell colony in the hybrid gel between the Type I and the Type IV extracted with an enzyme of Production Example 2 of Comparative Example 2; and FIG. 7D shows the ES cell colony in the "Matrigel".

As shown in FIG. 7A, relatively small number of large colonies was formed in the Type I collagen gel. On the other hand, as shown in FIG. 7B, many relatively small-size colonies were formed in the Type I-Type IV collagen hybrid gel of the present invention, and it was clarified that response of the ES cell differed by blending of the Type IV collagen having gelling ability.

(2) The gel of FIG. 7C is the Type IV hybrid gel not having Type I gelling ability. The colony of FIG. 7C differs from the colony of FIG. 7B in that relatively large colonies are scattered. The colony of FIG. 7B is the Type I-Type IV collagen hybrid gel of the present invention, and is clarified to have different response of the ES cell on the Type I-Type IV collagen hybrid gel depending on an extraction method of Type IV collagen. In particular, the gel of FIG. 7C is different from the gel of FIG. 7A, in containing the Type IV collagen not having gelling ability, however, both colonies are common in that relatively large colonies are scattered. This means that response of the ES cell incurred by the Type I-Type IV collagen hybrid gel of the present invention is not observed in the hybrid gel between the Type IV collagen extracted with an enzyme used in FIG. 7C and the Type I collagen.

(3) FIG. 7D shows a colony of the ES cell cultured by the "Matrigel", and the gel is blended with laminin, heparan sulfate proteoglycan, entactin and the like, which are constituents of the basement membrane, and have been known to have function to support adhesion of the epithelial cell and function to maintain a differentiation phenotype or the like. The colony of FIG. 7D is common to the colony of FIG. 7B in that small colonies are present in a scattered state. This means that the Type I-Type IV collagen hybrid gel of the present invention itself can induce ES cell response similar to the gel blended with a basement membrane component.

Analysis of Expression of a Differentiation Marker Gene of the Mouse ES Cell (1) On the mouse ES cell, the ES cell cultured in Example 6, and the ES cell cultured in Comparative Example 4, expression of Oct-3/4, which is a marker of a non-differentiated ES cell; Fgf5, which is an initial stage epiblast (ectoderm) differentiation marker; and Flk1, which is a mesoderm differentiation marker, was observed. FIG. 8A, FIG. 8B, and FIG. 8C are drawing which show expression of Oct-3/4, Fgf5 and Flk1, respectively. It should be noted that, in FIG. 8, reference letter 1 shows the mouse ES cell; reference letter 2 shows the ES cell cultured by the Type I collagen gel of Comparative Example 1; reference letter 3 shows the ES cell cultured by the hybrid gel between the Type I collagen and the Type IV collagen having gelling ability of Example 6; reference letter 4 shows the ES cell cultured by the hybrid gel between the Type I collagen and the Type IV collagen not having gelling ability of Comparative Example 2; and reference letter 5 shows the ES cell cultured by the commercial "Matrigel".

As shown in FIG. 8A, expression of Oct-3/4, which is a maker of a non-differentiated ES cell, was lower than the ES cell in any gel. It is suggested that differentiation of the ES cell was promoted in the case of using any gel.

(2) As shown in FIG. 8B, expression of Fgf5, which is an initial epiblast (ectoderm) marker, was introduced strongly by the hybrid gel (Example 6) of the Type I collagen and the Type IV collagen having gelling ability and the "Matrigel". In "Matrigel", laminin, heparan sulfate proteoglycan, entacti or the like, which have been known to have function to maintain a differentiation phenotype or the like, is blended, and it was suggested that the Type IV collagen having gelling ability has differentiation promoting ability to ectoderm similar to components thereof.

On the other hand, in the Type I collagen gel (Comparative Example 1) and the hybrid gel (Comparative Example 2) of the Type I collagen and the Type IV collagen extracted with an enzyme, expression of Fgf5 remained at a low level. This suggests that differentiation promoting ability to ectoderm by the Type IV collagen extracted with an enzyme is the same level as the Type I collagen.

(3) As shown in FIG. 8C, expression of Flk1, which is a differentiation maker to mesoderm, was suppressed in the hybrid gel (Example 6) of the Type I collagen and the Type IV collagen having gelling ability and the "Matrigel", and the expression was enhanced in the Type I collagen and the hybrid gel (Comparative Example 2) of the Type I collagen and the Type IV collagen extracted with an enzyme. This suggests that the Type I collagen has differentiation promoting ability to mesoderm, and also the Type IV collagen extracted with an enzyme has differentiation promoting ability to mesoderm similar to the Type I collagen.

(4) In comparing FIG. 8A, FIG. 8B and FIG. 8C, both of the Type I collagen (Comparative Example 1) and the hybrid gel (Comparative Example 1) of the Type I collagen and the Type IV collagen extracted with an enzyme tend to have similar expression amount of Oct-3/4, Fgf5 and Flk1. In addition, the hybrid gel (Example 6) of the Type I collagen and the Type IV collagen having gelling ability and the "Matrigel" tend to have similar expression amount of the three kinds. This shows that the Type IV collagen blended in the Type I collagen differs in physiological activity to differentiation of the ES cell, depending on an extraction method. In particular, there was feature in that, by extracting the Type IV collagen in a non-enzymatic way, differentiation ability similar to the "Matrigel", containing a basement membrane component, is exerted.

The invention claimed is:

1. A Type I-Type IV collagen hybrid gel prepared by mixing a Type 1 collagen having fibrosis ability and a Type IV collagen having gelling ability,
   wherein a membrane-like substance of the Type IV collagen is bound to a fibrous structure of the Type I collagen.

2. The Type I-Type IV collagen hybrid gel according to claim 1, wherein 100 to 500 parts by the Type I collagen is mixed to make the collagen hybrid gel, based on 100 parts by mass of the Type IV collagen.

3. The Type I-Type IV collagen hybrid gel according to claim 1 or 2, characterized by further comprising a laminin.

4. A cell culture plate, characterized in that the Type I-Type IV collagen hybrid gel according to claim 1 is coated onto a support for cell culture.

5. An artificial basement membrane, comprising the Type I-Type IV collagen hybrid gel according to claim 1.

6. A method for producing a Type I-Type IV collagen hybrid gel, comprising:
   preparing a hybrid collagen solution by mixing 100 to 500 parts by mass of a Type I collagen solution having fibrosis ability with a concentration of 0.05 to 10 mg/ml, based on 100 parts by mass of a Type IV collagen solution having gelling ability with a concentration of 0.05 to 10 mg/ml, at a temperature of 0 to 4° C.;
   adjusting the osmotic pressure of the hybrid collagen solution from 0.5 to 2 times to that of human body fluid at a neutral pH and at a temperature of 0 to 4° C.; and then
   forming a three-dimensional gel by incubating at a temperature of 30 to 40° C. for 10 minutes to 2 hours, under $CO_2$ condition.

7. The method for producing the Type I-Type IV collagen hybrid gel according to claim 6, characterized in that incubating is carried out at a temperature of 30 to 40° C. for 1 to 24 hours, by further adding the laminin to the three-dimensional gel so as to be a concentration of 10 to 200 µg/ml.

8. A method for producing a cell culture plate, comprising:
   producing a hybrid collagen solution by mixing 100 to 500 parts by mass of a Type I collagen solution having fibrosis ability with a concentration of 0.05 to 10 mg/ml, based on 100 parts by mass of a Type IV collagen solution having gelling ability with a concentration of 0.05 to 10 mg/ml, at a temperature of 0 to 4° C.;
   adjusting the osmotic pressure of the hybrid collagen solution is adjusted osmotic pressure from 0.5 to 2 times to that of human body fluid at a neutral pH and at a temperature of 0 to 4° C.; and then
   forming a three-dimensional gel by putting the resultant solution on a support for cell culture plate and incubating at a temperature of 30 to 40° C. for 10 minutes to 2 hours, under $CO_2$ condition.

9. The method for producing the cell culture plate according to claim 8, characterized in that incubating is carried out at a temperature of 30 to 40° C. for 1 to 24 hours, by further adding the laminin to the three-dimensional gel, so as to be a concentration of 10 to 200 µg/ml, subsequent to formation of the three-dimensional gel.

10. A method for producing an artificial basement membrane, comprising:
   preparing a hybrid collagen solution by mixing 100 to 500 parts by mass of a Type I collagen solution having fibrosis ability with a concentration of 0.05 to 10 mg/ml, based on 100 parts by mass of a Type IV collagen solution having gelling ability with a concentration of 0.05 to 10 mg/ml, at a temperature of 0 to 4° C.;
   adjusting the osmotic pressure of the hybrid collagen solution from 0.5 to 2 times to that of human body fluid at a neutral pH and at a temperature of 0 to 4° C.;
   forming a three-dimensional gel by coating the resultant solution on a flat plate and incubating at a temperature of 30 to 40° C. for 10 minutes to 2 hours, under $CO_2$ condition, to obtain a thickness of 0.01 to 3 mm; and then recovering the three-dimensional gel from the flat plate.

11. The method for producing the artificial basement membrane according to claim 10, characterized in that incubating is carried out at a temperature of 30 to 40° C. for 1 to 24 hours, by adding laminin to the three-dimensional gel, so as to be a concentration of 10 to 200 µg/ml, subsequent to formation of the three-dimensional gel.

* * * * *